United States Patent [19]

Carpino et al.

[11] Patent Number: 5,536,815
[45] Date of Patent: Jul. 16, 1996

[54] CYCLOPROPYL BASED O- AND N- AND S-PROTECTING GROUPS

[75] Inventors: Louis A. Carpino, Amherst, Mass.; Hann-Guang Chao, Lawrenceville, N.J.

[73] Assignee: Research Corporation Technologies, Inc., Tucson, Ariz.

[21] Appl. No.: 221,226

[22] Filed: Mar. 31, 1994

[51] Int. Cl.$^6$ .................... C07C 229/06; C07C 229/12; C07C 321/04; C07K 1/06
[52] U.S. Cl. ............... 530/335; 530/336; 530/337; 548/339.1; 548/496; 562/445; 562/557; 562/560; 562/562; 562/563; 562/567; 562/570; 562/571; 562/573
[58] Field of Search ..................... 530/335, 336, 530/337; 548/339.1, 496; 562/445, 557, 560, 561, 562, 563, 567, 570, 571, 573

[56] References Cited

U.S. PATENT DOCUMENTS

| | | | |
|---|---|---|---|
| 4,565,819 | 1/1986 | Vincent et al. | 546/147 |
| 4,622,417 | 11/1986 | Barnett et al. | 530/801 |
| 4,638,071 | 1/1987 | Barnett et al. | 560/116 |
| 4,692,512 | 9/1987 | Janusz | 514/773 |
| 4,692,513 | 9/1987 | Blum et al. | 514/773 |
| 4,781,927 | 11/1988 | Zanno et al. | 426/548 |

FOREIGN PATENT DOCUMENTS

| | | | |
|---|---|---|---|
| 1205121 | 9/1970 | United Kingdom | 530/336 |

OTHER PUBLICATIONS

Brady et al. "Some Novel, Acid–Labile Amine Protecting Groups", *Journal of Organic Chemistry*, 1977, 42, 143–146.
J. Med. Chem., vol. 35, No. 6, Issued 1992, Olken et al., "N$^G$–Allyl— and N$^G$–Cyclopropyl–L–Arginine", pp. 1137–1144.
W. J. Close (1956) "An Improved Synthesis of Cyclopropyl Phenyl Ketone and Related Substances", *JACS 79*, 1455–1458.
Louis A. Carpino (1993) "1-Hydroxy-7-azabenzotriazole. An Efficient Peptide Coupling Additive", *J. Am. Chem. 115*, 4397–4398.
Eckenberg et al. (1993) "A Useful Application of Benzyl Trichloroacetimidate for the Benzylation of Alcohols", *Tetrahedron 49*, 1619–1624.
Timberlake et al. (1986) "Synthetic Routes to Cyclopropyl-–Substituted Azoalkanes. Some Reactions of Cyclopropylcarbinyl Cyanates, Isocyanates, Benzoates, and p–Nitrobenzoates", *J. Org. Chem. 33*, 4054–4060.
William D. Lubell et al. (1988) "α–Amino Acids as Chiral Educts for Asymmetric Products. Alkylation of N–Phenylfluorenyl α–Amino Ketones. Synthesis of Optically Pure α–Alkyl Carboxylic Acids", *J. Am. Chem. Soc. 110*, 7447–7455.
A. I. Meyers et al. (1978) "Asymmetric Synthesis of (+) or (–)-2–Methyloctanal via the Metallocnamines of Chiral Alkoxy Amines", *J. Org. Chem. 43*, 892–898.
Brown et al. (1977) "Structural Effects in Solvolytic Reactions. 19. the Relative Electron Releasing Capability of Methyl, Phenyl, and Cyclopropyl Groups as Measured by the Tool of Increasing Electron Demand", *J. Org. Chem. 42*, 1073–1076.
Carpino et al. (1990) "(9–Fluorenylmethyl)oxy)carbonyl (FMOC) Amino Acid Fluorides. Convenient New Peptide Coupling Reagents Applicable to the FMOC/tert–Butyl Strategy for Solution and Solid–Phase Syntheses", *J. Am. Chem. Soc. 112*, 9651–9652.
Carpino et al. (1989) "Investigation of the Reaction between Amino Acids or Amino Acid Esters and 9–Formylfluorene and Its Equivalents. Possible Utility of the Derived Enamines as Amino Group Protectants", *J. Org. Chem. 54*, 4302–4313.
Carpino et al. (1989) "Tris(2–aminoethyl)amine as a Substitute for 4–(Aminomethyl)piperidien in the FMOC/Polyamine Approach to Rapid Peptide Synthesis", *J. Org. Chem. 55*, 1673–1675.
Akaji et al. (1990), "Fmoc–based Solid–phase Peptide Synthesis using a New t-Alcohol Type 4–(1', 1'–dimethyl–1'–hydroxypropopyl)phenoxyacetyl Handle (DHPP)–Resin (Fmoc=fluoren–9–ylmethoxycarbonyl)", *J. Chem. Soc.*, 584–586.
Pocar et al. (1975) "Enamines–XXXIX Enamines from Cyclopropylketones", *Tetrahedron 31*, 2427–2429.

Primary Examiner—Jeffrey E. Russel
Attorney, Agent, or Firm—Scully, Scott, Murphy & Presser

[57] ABSTRACT

The present invention is directed to the use of a cyclopropylmethyl derivative as a protecting group for compounds containing an amino group, carboxy group, amido group, mercapto group or hydroxy group and to the compounds formed having the cyclopropylmethyl moiety as the protecting group.

112 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide (xi) SEQUENCE DESCRIPTION: SEQ ID NO:1:

Trp Ala Gly Gly Asp Ala Ser Gly Glu
1               5

(2) INFORMATION FOR SEQ ID NO:2:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..6
(D) OTHER INFORMATION: /label=ProtectingGrps
/ note="N-terminus Gly has FMOC protecting group, Asp has O-t-Bu protecting group, Ser has t-Bu protecting group and Glu at C-terminus has two O-t-Bu protecting groups.

(xi) SEQUENCE DESCRIPTION: SEQ ID NO:2:

Gly Asp Ala Ser Gly Glu
1           5

(2) INFORMATION FOR SEQ ID NO:3:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..9
(D) OTHER INFORMATION: /label=ProtectingGrps
/ note="N-terminus Trp contains BOC protecting group, Asp contains O-t- Bu protecting group, Ser has t-Bu protecting group and C- terminus Glu has two O-t-Bu protecting groups.

(xi) SEQUENCE DESCRIPTION: SEQ ID NO:3:

Trp Ala Gly Gly Asp Ala Ser Gly Glu
1               5

CYCLOPROPYL BASED O- AND N- AND S-PROTECTING GROUPS

GOVERNMENT SUPPORT

This work has been supported by a grant from the National Institutes of Health GM 09706. The Government has certain rights in the invention.

FIELD OF THE INVENTION

The present invention relates to a new method for protecting carboxy, mercapto, hydroxy, amino or amide groups in organic molecules and to the protected products formed therefrom. The protecting groups contain a cyclopropylmethyl moiety and is cleaved under mild conditions. In addition, the present invention relates to a new method for protecting amino acids during peptide synthesis. More specifically, protecting groups containing the cyclopropylmethyl moiety are effective for protecting the carboxy groups on the amino acid; said carboxy group may be on the main chain or on the side chain. Furthermore, this protecting group is effective for protecting amino groups, either on the main chain or the side chain of an amino acid as well as amido, hydroxy, and mercapto groups on the side chain of an amino acid. The protecting groups of the present invention prevent the amido, carboxy, amino, mercapto or hydroxy groups from undergoing undesirable side reactions during peptide synthesis.

BACKGROUND OF THE INVENTION

Polypeptides, including proteins, have become increasingly important in various health related fields. For example, in recent years, peptides have been found to be of pharmacological importance against various diseases, such as cancer, diabetes, plant toxins, and the like. Other polypeptides have shown specific activity as growth promoters or suppressants, antibiotics, insecticides, contraceptives, anti-hypotensives, sleep-inducers, anti-depressants, analgesics, etc. The list is long and varied.

The importance of polypeptides has sparked renewed interest in finding new methods for synthesizing polypeptides from amino acids or from smaller peptides.

A basic problem in peptide synthesis is one of blocking or protecting the carboxy group from interacting with an amino group on the same amino acid and/or preventing functional groups such as an amino group, carboxy group, hydroxy group, mercapto group or amido group on a side chain of an amino acid from undergoing undesirable reactions. The objective is to prevent undesirable side reactions by attaching to an amino acid a group that will render the above-identified substituents unreactive so as to permit the desired reaction to take place. In addition, the blocking group should be easily removed without destruction of any peptide linkage that may have been built during the synthesis.

Amino protecting groups such as FMOC and BOC have been widely used in peptide synthesis, especially solid phase peptide synthesis, including synthesis of peptide amides and peptide acid segments. In the case of protected peptide acids, the segments could be utilized in segment condensation utilizing either solution or solid phase techniques.

One of the methods to effect segment condensation involves the use of α-FMOC or BOC protection with side chain protection provided by t-butyl based functions (BOC, t-Bu-ether, t-Bu-ester) or benzyl based substituents, respectively. A potentially orthogonal approach involves the use of C-terminal carboxy protection by the allyl ester group with eventual cleavage by palladium catalyzed reactions. Such deblocking reactions are sensitive to traces of oxygen, and may be difficult to reproduce. Far more reliable and simpler to execute, however, is a system whereby a very mild acidic reagent is used to cleave the C-terminal ester linkage.

The present invention provides blocking groups which protect amino groups, amide groups, mercapto groups, hydroxy groups or carboxy groups from undergoing undesirable side reactions, especially during peptide synthesis, provides blocking groups which are easy to remove and provides a system wherein the results are easy to reproduce.

The key to the present invention involves recognition of the enhanced solvolytic behavior of the cyclopropyl methyl substrate. The present invention is directed to the use of the cyclopropylmethyl derivative in protecting various groups on an amino acid or peptide during peptide synthesis. These groups may be located on the main chain or on the side chain. These groups include amide, amino, carboxy, mercapto and hydroxy groups.

SUMMARY OF THE INVENTION

The present invention is directed to amino acids containing a cyclopropylmethyl as a protecting group. The present invention includes compounds having the formula:

$$\text{BLK}-\text{N}-\underset{R}{\overset{H}{\underset{|}{C}}}-\overset{O}{\underset{}{\overset{\|}{C}}}-X$$

wherein
R is one of the side chains of an α-amino acid;
BLK is an N-amino protecting group,

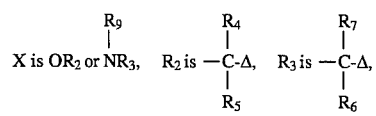

$R_9$ is H or lower alkyl,
$R_4$ is hydrogen or lower alkyl;
$R_7$ and $R_5$ are independently lower alkyl, aryl, aryl lower alkyl, lower cycloalkyl, lower cycloalkyl lower alkyl; and
$R_6$ is lower alkyl, aryl lower alkyl, aryl, lower cycloalkyl or lower cycloalkyl lower alkyl.

In the above formula, the cyclopropylmethyl group is protecting a carboxy or amide group on the main chain.

The present invention is also directed to α-amino acids containing the cyclopropylmethyl protecting group on the side chain. The cyclopropylmethyl group is used to protect the amino, mercapto, carboxy, amide, or hydroxy group thereon. Thus, the present invention is also directed to protected amino acids of the formula:

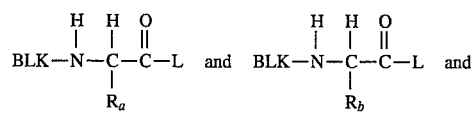

BLK is an amino protecting group;
L is halide, OH or $OR_8$;

$R_a$ is a side chain of an α-amino acid having a primary or secondary amino group and attached to said amino group is a moiety of the formula:

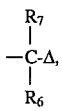

$R_b$ is a side chain of an amino acid, said side chain containing a carboxy, mercapto or hydroxy group, and attached to said group is a moiety of the formula:

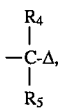

$R_8$ is lower alkyl, and $R_4$, $R_5$, $R_6$ and $R_7$ are as defined hereinabove.

The present invention is also directed to a method of protecting amino, amido, carboxy, hydroxy or mercapto groups on organic molecules, such as an amino acid, with a cyclopropylmethyl blocking group. With respect to protecting a carboxy group, a mercapto group, hydroxy group, the method comprises reacting the carboxy group or acylating derivative thereof, the mercapto or hydroxy group on the organic molecule with a compound of the formula:

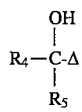

(b) modifying a portion of the molecule other than the protected group by chemical reaction, and (c) removing the protecting group.

If a primary or secondary amine is present on the organic molecule, the present invention protects the amine by (a) reacting said organic molecule containing the amine with a compound of the formula:

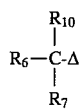

wherein $R_6$ and $R_7$ are as defined hereinabove and $R_{10}$ is a good leaving group such as halide, tosylate, mesylate, brosylate, and the like;

(b) modifying a portion of the molecule other than the protected group by chemical reaction and (c) removing the protecting group.

The present invention is also directed to a process for converting an organic molecule containing a carboxy group to an amide and protecting the amide thus formed. More specifically, the organic molecule containing the carboxy group or acylating derivative thereof is reacted with a compound of the formula:

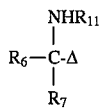

wherein $R_6$ and $R_7$ are as defined hereinabove and $R_{11}$ is hydrogen or lower alkyl, to form the cyclopropyl methyl protected amide, (b) the portion of the molecule other than the protected group is modified by chemical reaction and (c) the cyclopropylmethyl protecting group is subsequently removed. In all of these cases, the cyclopropyl methyl protecting group is removed under very mild conditions.

DETAILED DESCRIPTION OF THE INVENTION

As used herein, the term "lower alkyl" when used alone or in combination refers to an alkyl group containing 1–6 carbon atoms. The alkyl group may be straight-chained or branched. Examples include methyl, ethyl, propyl, isopropyl, butyl, t-butyl, sec-butyl, isobutyl, pentyl, isopentyl, neopentyl, hexyl, isohexyl and the like. The preferred alkyl group contains 1–3 carbon atoms.

"Lower alkylthio", as used herein, refers to a sulfur atom bridging the main chain with a lower alkyl. In other words, it is the group —S—lower alkyl.

"Lower alkoxy" as used herein, refers to O-lower alkyl substituent, wherein the O atom is attached to the main chain.

As used herein, lower alkanoyl refers to a lower alkyl group containing a carbonyl group. It is preferred that the carbonyl C

is attached directly to the main chain. Examples include acetyl, propanoyl, and the like.

As used herein, "carbo lower alkoxy" refers to COO-lower alkyl, wherein the carbonyl group

is attached to the main chain. Examples include carbomethoxy, carboethoxy, and the like.

A leaving group as defined herein, is a group that is cleaved of a molecule in a substitution reaction. Examples include halide, aryl or lower alkyl sulfonic ester derivatives, such as tosylates, brosylates, mosylates, mesylates (—$OSO_2$—J, wherein J is halo, aryl, lower alkyl, lower alkyl), betylates, triflates, nonaflates, tresylates and the like.

The term "aryl" refers to an aromatic ring system containing 6–14 ring carbon atoms and up to a total of 22 carbon atoms. Examples include phenyl, α-naphthyl, β-naphthyl, and the like. Phenyl is the most preferred aryl group.

The term "aryl lower alkyl" refers to a substituent containing an aryl and alkyl group as defined herein, wherein the alkyl group is attached to the main chain. The aryl lower alkyl group may contain from 7 to 25 carbon atoms, but, it is preferred to contain 7–10 carbon atoms. Examples include benzyl, phenethyl, phenpropyl, naphthylmethyl, and the like.

Lower cycloalkyl, as defined herein, refers to a cycloalkyl group containing 3–10 ring carbon atoms. The cycloalkyl group may be completely saturated or may be partially saturated. If it contains multiple bonds, it is preferred that the multiple bonds are double bonds. The cycloalkyl group may contain 1, 2, or 3 double bonds. The cycloalkyl groups may contain some aromatic character, but cannot be fully aromatic. The cycloalkyl group may contain more than one ring, and thus may be monocyclic, bicyclic or tricyclic. It is preferred that the cycloalkyl group contains 1 or 2 rings. If more than one ring is present, it is preferred that the rings are fused. The preferred cycloalkyl groups are saturated. Furthermore, the preferred cycloalkyl groups contain 3–6 ring carbon atoms. Especially preferred are the saturated cycloalkyl containing 3–6 carbon atoms. Examples include cyclopropyl, cyclobutyl, cyclopentyl, cyclohexyl, cycloheptyl, cyclooctyl, cyclononyl, decahydronaphthyl, cyclohexenyl, adamantyl, indanyl, and the like. The preferred cycloalkyl group is cyclopropyl.

The term lower cycloalkyl lower alkyl refers to a substituent containing a lower cycloalkyl group and a lower alkyl group, as defined herein, wherein the alkyl moiety is attached directly to the main chain. In other words, the alkyl bridges the cycloalkyl group and the main chain. The lower cyclo alkyl group may contain from 4 to 25 carbon atoms, but it is preferred that it contains 4 to 12 carbon atoms.

Each of the groups defined hereinabove may be unsubstituted or may be substituted with alkyl groups, electron donating groups, or electron withdrawing groups. As used herein, an electron donating group shall designate a group that will release or donate electrons more than hydrogen would if it occupied the same position in the molecule. See, J. March, *Advanced Organic Chemistry*, 3rd Edition, John Wiley & Sons, p. 238 (1981). These types of groups are well known in the art. Examples include aryl, aryl lower alkyl, lower alkylthio, lower alkoxy, lower aralkoxy, and the like.

The term "electron withdrawing groups" as defined herein refers to a group that will draw electrons to itself more than a hydrogen would if it occupied the same position in the molecule. See, J. March, *Advanced Organic Chemistry*, 3rd Edition, John Wiley & Sons, p. 17 (1985). These types of groups are also well known in the art. They include such groups as nitro, monohaloloweralkyl, dihalo loweralkyl, trihalo loweralkyl (e.g. $C_3$), halo, formyl, lower alkanoyl, carbo lower alkoxy, and the like. Preferred electron withdrawing groups are halo, formyl and lower alkanoyl.

Examples of an acylating derivative of an amino acid, as used herein, refers to the amino acid, ester, amide, acid halide, anhydride thereof, and the like. The preferred acylating derivatives are the amino acid, aryl esters of the mono acid, lower aryl alkyl esters of the amino acid, lower cycloalkyl esters of the amino acids, amino acid halides and the like. Especially preferred are the amino acid halides.

As used herein, the term "amino acid" refers to an organic acid containing both a basic amino group ($NH_2$) and an acidic carboxyl group (COOH). Therefore, said molecule is amphoteric and exists in aqueous solution as dipole ions. (See, "The Condensed Chemical Dictionary:, 10th Ed. edited by Gessner G. Hawly, Van Nostrand Reinhold Company, London, Engl. p. 48 (1991).) The preferred amino acids are the α-amino acids. Even more preferred are the naturally occurring α-amino acids. They include but are not limited to the 25 amino acids that have been established as protein constituents. They include such proteinogenic amino acids as alanine, valine, leucine, isoleucine, norleucine, proline, hydroxyproline, phenylalanine, tryptophan, methionine, glycine, serine, threonine, cysteine, cystine, tyrosine, asparagine, glutamine, aspartic acid, glutamic acid, lysine, hydroxylysine, ornithine, arginine, histidine, penicillamine and the like. As used herein, the amino acid also includes amino acid containing protecting groups as described hereinbelow.

An "amino acid residue", as defined herein, is an amino acid minus an amino hydrogen on the amino end of the molecule and the OH group on the carboxy end of the molecule (i.e., it includes the carbonyl group

on the carboxy end of the molecule). Therefore, unless designated to the contrary, the group "AA" as part of a peptide signifies an amino acid residue. For example, the amino acid residues of various amino acids are represented below:

| AA Symbol | AA Residue |
|---|---|
| Gly | —NH—CH₂—C(=O)— |
| Ala | —NH—CH(CH₃)—C(=O)— |
| Leu | —NH—CH(CH₂CH(CH₃)₂)—C(=O)— |
| Ile | —NH—CH(CH(CH₃)CH₂CH₃)—C(=O)— |
| Pro | (pyrrolidine)—C(=O)— |
| Phe | —N(H)—CH(CH₂—C₆H₅)—C(=O)— |
| Trp | —HN—C(H)(CH₂-indolyl)—C(=O)— |
| Met | —HN—CH((CH₂)S—CH₃)—C(=O)— |
| Ser | —HN—CH(CH₂OH)—C(=O)— |

| AA Symbol | AA Residue |
|---|---|
| Thr | −HN−CH(CH(OH)CH$_3$)−C(=O)− |
| Cys | −HN−CH(CH$_2$SH)−C(=O)− |
| Tyr | −HN−CH(CH$_2$−C$_6$H$_4$−OH)−C(=O)− |
| Asn | −NH−CH(CH$_2$−CONH$_2$)−C(=O)− |
| Gln | −HN−CH((CH$_2$)$_2$−CONH$_2$)−C(=O)− |
| Asp | −HN−CH(CH$_2$−COOH)−C(=O)− |
| Glu | −HN−CH((CH$_2$)$_2$−COOH)−C(=O)− |
| Lys | −HN−CH((CH$_2$)$_4$NH$_2$)−C(=O)− |
| Arg | −HN−CH(CH$_2$CH$_2$CH$_2$NH−C(=NH)−NH$_2$)−C(=O)− |
| His | −HN−CH(CH$_2$−imidazolyl)−C(=O)− |
| Nor | −HN−CH((CH$_2$)$_2$CH$_3$)−C(=O)− |

The term N-α-amino acid protecting groups, as used herein, refers to blocking groups which are known in the art and which have been utilized to block the amino (NH$_2$) group of the amino acid. Blocking groups such as 9-lower alkyl-9-fluorenyloxycarbonyl,2-chloro-1-indanylmethoxycarbonyl (CLIMOC) and benz [f] indene-3-methoxycarbonyl (BIMOC) and dbd-TMOC are discussed in U.S. Pat. Nos. 3,835,175, 4,508,657, 3,839,396, 4,581,167, 4,394,19, 4,460,501 and 4,108,846, and the contents thereof are incorporated by reference as if fully set forth herein. Moreover, other amino protecting groups such as 2-(t-butyl sulfonyl)-2-propenyloxycarbonyl (BSPOC) and benzothiophene sulfone-2-methylcarbonyl (BSMOC) are discussed in U.S. Pat. No. 5,221,754 and the subject matter therein is incorporated herein by reference. Other amino protecting groups are described in an article entitled "Solid Phase Peptide Synthesis" by G. Barany and R. B. Merrifield in *Peptides*, Vol. 2, edited by E. Gross and J. Meinenhoffer, Academic Press, New York, N.Y., pp. 100–118 (1980), the contents of which are incorporated herein by reference. The N-α-amino protecting groups referred to in the present application include such groups as the FMOC, Bspoc, Bsmoc, t-butyloxycarbonyl (BOC), t-amyloxycarbonyl (Aco), β-trimethylsilylethyloxycarbonyl (TEOC), adamantyloxycarbonyl (ADOC), 1-methylcyclobutyloxycarbonyl (MCB), 2-(p-biphenylyl)propyl-2-oxycarbonyl (BPOC), 2-(p-phenylazophenyl)propyl-2-oxycarbonyl (AZOC), 2-2-dimethyl-3,5-dimethyloxybenzyloxycarbonyl (DDZ), 2-phenylpropyl-2-oxycarbonyl (POC), benzyloxycarbonyl (CBZ), p-toluenesulfonyl aminocarbonyl (TAC), o-nitrophenylsulfenyl (NPS), dithiasuccinoyl (DTS), phthaloyl, piperidinooxycarbonyl, formyl, trifluoroacetyl and the like. The preferred BLK groups are BOC, BSMOC, FMOC and CBZ.

Abbreviations have been used in the specification with respect to these blocking groups and are listed hereinbelow:

| Protecting group | Abbreviation |
|---|---|
| dimethoxybenzhydryl | DMB |
| 2,4,6-trimethoxybenzyl | TMB |
| 2,3,6-trimethyl-4 methoxybenzenesulfonyl | MTR |
| 9-fluorenylmethyloxycarbonyl | FMOC |
| t-butoxycarbonyl | BOC |
| t-butoxymethyl | BOM |
| pentamethylchromanesulfonyl | PMC |
| adamantyl | ADA |
| β-trimethylsilylethyl | TMSE |
| β-trimethylilylethyloxycarbonyl | TEOC |
| t-butyl | t-Bu |
| benzyl | BZ |
| cyclopentyl | CP |
| cyclohexyl | CH |
| triphenylmethyl | TRT |
| benzyloxycarbonyl | CBZ or Z |
| adamantyloxycarbonyl | ADOC |
| formyl | CHO |
| trifluoroacetyl | TFA |

These protecting groups can be placed into five categories:

1) a base labile Nα-amino acid protecting group such as FMOC, and the like.
2) protecting groups removed by acid, such as BOC, TEOC, AOC, ADOC, MCB, BPOC, AZOC, DDZ, POC, CBZ, 2-furanmethyloxycarbonyl (FOC), p-methoxybenzyloxycarbonyl (MOZ), NPS, and the like.
3) protecting groups removed by reduction or catalytic hydrogenation such as DTS, CBZ.
4) protecting groups removed by nucleophiles, such as BSPOC, BSMOC, NPS and the like.
5) protecting groups derived from carboxylic acids, such as formyl, acetyl, trifluoracetyl and the like, which are removed by acid, base or nucleophiles.

As defined herein, a nucleophile is an electron-rich atom, i.e., an atom which can donate an electron pair, which tends to attack a carbon nucleus but does not act as a Bronsted Lowry base.

As used herein, the term "peptide" refers to the class of compounds composed of amino acid units chemically bound together with amide linkages. A peptide may contain as little as two amino acid residues or may contain a polymer of amino acid residual polypeptides.

The term "amino acid" and "peptide" also includes amino acids and peptides, respectively, containing blocking (protecting) groups. The protecting groups block the portions of the amino acid or peptide containing functional groups, such as carboxy, hydroxy, amino, amido, mercapto, and the like which may be reactive under the reaction conditions but are not involved in or taking part in the coupling reaction in order to prevent unwanted side reactions. These protecting groups protect reactive groups on the main and side chain of the amino acids or peptides.

As used herein, unless indicated to the contrary, the term protecting groups include the N-∝-amino protecting groups. Also included are the ∝-carboxy protecting groups. It also includes the side chain protecting groups indicated hereinbelow.

It will be apparent to one skilled in the art that in the course of protein synthesis, it may be necessary to protect certain side chains of the amino acids to prevent unwanted side reactions. For example, it may be necessary to protect the hydroxyl group on the side chain of tyrosine, serine, or threonine with the desired reactions. This is a common problem in peptide synthesis and many procedures are available for amino acids. Such procedures for protecting various functional groups are known to one skilled in the art and are described in the treatise entitled "The Peptides", Vol. 2, Edited by E. Gross and J. Meinenhoffer, Academic Press, NY, N.Y., pp. 166–251 (1980), and the book entitled "Protective Groups in Organic Synthesis", by T. W. Green, John Wiley and Sons, New York, 1981, the contents of both being incorporated herein by reference.

For example, when the functional side chain contains a hydroxy group, such as threonine or serine, it can be protected by such groups as methyl, methoxymethyl (MOM), 2-methoxyethoxymethyl (MEM), tetrahydropyranyl, B-trimethylsilylethyl, 4-methoxytetrahydropyranyl, 1-ethoxyethyl, t-butyl, p-methoxybenzyl, p-halobenzyl, o-nitrobenzyl, p-nitrobenzyl, o-chlorobenzyl, adamantyl, diphenylmethyl, triphenylmethyl, cyclohexyl, cyclopentyl, 1-benzyloxycarbonyl, tri-substituted silyl, wherein the substituents are independently aryl, alkyl or aralkyl, 2,2,2-trifluoroethyl, and the like.

When the side chain contains a phenol, such as in tyrosine, it may be protected by such groups as methyl, methoxymethyl(MOM), methoxyethoxymethyl(MEM), β-trimethylsilylethyl, methylthiomethyl, tetrahydropyranyl, isopropyl, cyclohexyl, cyclopentyl, t-butyl, adamantyl, 4-methoxybenzyl, o-nitrobenzyl, 2,4-dinitrophenyl, m-bromobenzyl, 2,6-dichlorobenzyl, trisubstituted-silyl wherein the substituents are independently alkyl, aryl or aralkyl, ethoxycarbonyl, carbamoyl and the like.

A carboxy side chain, such as that found in aspartic acid or glutamic acid, can be protected by the following groups: 1- or 2-adamantyl, methoxymethyl, methylthiomethyl, t-butyl, methyl, ethyl, phenyl, tetrahydropyranyl, cyclopentyl, cyclohexyl, cycloheptyl, 4-picolyl, trisubstituted-silyl wherein the substituents are independently alkyl, aryl or aralkyl, N-piperidinyl, N-succinimidoyl, β-trimethylsilylethyl, 4-methoxybenzyl, benzyl, p-bromobenzyl, p-chlorobenzyl, p-nitrobenzyl, phenacyl, N-phthalimidoyl, 4-alkyl-5-oxo-1,3-oxazolidinyl, trisubstituted-stannyl wherein the substituents are independently alkyl, aryl or aralkyl, and the like.

If the functional group on the side chain is mercapto, e.g., cysteine, such groups as triphenylmethyl, benzyl, 4-methylbenzyl, 3,4-dimethylbenzyl, 4-methoxybenzyl, β-trimethylsilylethyl, p-nitrobenzyl, 4-picolyl, diphenylmethyl, triphenylmethyl, bis(4-methoxyphenyl)methyl, diphenyl-4-pyridylmethyl, 2,4-dinitrophenyl, t-butyl, t-butylthio, adamantyl, isobutoxymethyl, benzylthiomethyl, thiazolindinyl, acetamidomethyl, benzamidomethyl, 2-nitro-1-phenylethyl, 2,2-bis(carboethoxy)ethyl, 9-fluorenemethyl, acetyl, benzoyl, and the like can be used to protect said group.

If the side chain contains an amino group, such as the ε-amino group of lysine and ornithine, the following groups may be used: 9-fluorenylmethyloxycarbonyl, 9-(2-sulfo)fluorenylmethyloxycarbonyl, β-trimethylsilylethyloxycarbonyl, 2-furanylmethoxycarbonyl, adamantyloxycarbonyl, carbobenzoxy, t-butyloxycarbonyl, t-amyloxycarbonyl, cyclobutyloxycarbonyl, 1-methylcyclobutyloxycarbonyl, cyclopentyloxycarbonyl, cyclohexyloxycarbonyl, 1-methylcyclohexyloxycarbonyl, cyclopentyloxycarbonyl, cyclohexyloxycarbonyl, 1-methylcyclohexyloxycarbonyl, isobornyloxycarbonyl, benzyl, p-methoxybenzyloxycarbonyl, p-nitrobenzyloxycarbonyl, chlorobenzyloxcarbonyl, isonicotinyloxycarbonyl, p-toluenesulfonylamidocarbonyl, methylsulfonylethyloxycarbonyl, β,β,β-trichloroethyloxycarbonyl, dithiasuccinoyl, phthaloyl, 4,5-diphenyl-4-oxazoline-2-one, piperidino oxycarbonyl trifluoracetyl, chloroacetyl, p-toluenesulfonyl and the like.

If the amino acid has an imidazole group, such as in histidine, the following groups may be used to protect the side chain: benzyloxymethyl, piperidinylcarbonyl, phenacyl, pivaloyloxymethyl, 1-(alkoxycarbonylamino)-2,2,2-trifluorethyl, 1-trifluormethyl-1-(p-chlorophenoxymethoxy)-2,2,2trifluorethyl, 2,4-dinitrophenyl, toluenesulfonyl, FMOC, triphenylmethyl, t-butyloxycarbonyl, and the like.

When the amino acid has a guanidine side chain, such as in arginine, the following protecting groups can be used to protect the ω nitrogen on the guanidine moiety: methoxytrimethylbenzenesulfonyl, pentamethylchromanesulfonyl, mesitylenesulfonyl, toluenesulfonyl, 2,4,6-trimethylbenzenesulfonyl, trimethoxybenzenesulfonyl, bisadamantyloxylcarbonyl, nitro, tosyl, and the like.

For side chains containing an amide group such as in glutamine and asparagine, the following groups can be used to protect the side chain; dimethoxybenzylhydryl, 9-xanthenyl, 2,4,6-trimethoxybenzyl, and the like.

To distinguish between the protecting groups described hereinabove and those of the present invention, the term "cyclopropylmethyl protecting group" will be utilized.

However, it is within the scope of the present invention to have amino acids or peptides having one or more protecting groups present. The amino acids or peptides of the present invention contain at least one cyclopropylmethyl protecting group as defined herein. However, if more than one protecting group is present, the other one(s) may be a cyclopropylmethyl protecting groups described herein or one of the other protecting groups enumerated hereinabove, or a combination thereof.

The present invention is directed to the cyclopropylmethyl based protected amino acids, as defined hereinabove. As defined herein, the cyclopropyl methyl based protecting groups as used to protect, inter alia, the α-carboxy group on the amino acid. Obviously this protecting group is used when the carboxylic acid group is not involved in the reaction. If the side chain has a functional group, i.e., a group capable of reacting under the conditions of the reaction, then the protecting group on the side chain should also be protected. In the situation wherein the α-carboxy group is protected by the cyclopropylmethyl moiety, the side chain may be protected by the protecting groups enumerated hereinabove or by a cyclopropylmethyl protecting group.

The present invention is also directed to protecting certain functional groups in the side chain, i.e., an amino, amido, mercapto, hydroxy, or carboxy group. Thus, under these circumstances, the side chain may have the cyclopropylmethyl protecting group and the main chain may have a protecting group enumerated herein on the N-∝-amino group or a common protecting group on the ∝-carboxy or it may have a cyclopropyl methyl protecting group of the present invention. In fact, the present invention contemplates amino acids and peptides having just the cyclopropyl methyl derivatives as the sole protecting groups as well as all combinations and permutations of protecting groups described hereinabove with the cyclopropylmethyl protecting groups on the functional groups on the main or side chain of the amino acid residue, as long as one of the protecting groups thereon is a cyclopropylmethyl protecting group.

Thus, the present invention is directed to compounds of the formula $$\text{BLK}-\overset{H}{\underset{}{N}}-\overset{H}{\underset{R}{C}}-\overset{O}{\overset{\|}{C}}-X$$

wherein BLK and X is as defined herein and R is the side chain of the amino acid. If the side chain has a functional group, then it may be protected and the protecting group may be any of the groups enumerated hereinabove. Or, if the side chain has a hydroxy, amino, amido, carboxy or mercapto, it may be protected by one of the cyclopropylmethyl groups defined herein, as discussed hereinbelow.

If it is desired to protect the carboxy group, then X is $OR_2$, wherein $R_2$ is

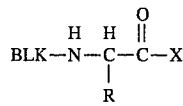

and $R_4$ and $R_5$ are as defined hereinabove. Although $R_4$ is hydrogen or lower alkyl, it is preferred that $R_4$ is hydrogen. Furthermore, it is preferred that $R_5$ is cycloalkyl, aryl or lower alkyl. Aryl, e.g. phenyl, and cycloalkyl are the more preferred substituents, and cycloalkyl, especially cyclopropyl is the most preferred. The preferred BLK are BOC, FMOC, BSMOC or CBZ.

When X is $NR_3$ and $R_3$ is

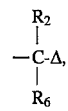

then the compound of Formula I becomes a cyclopropyl methyl protected amide of the amino acid. In this embodiment, the preferred BLK is as described hereinabove, viz, BOC, BSMOC and CBZ. In addition, it is preferred that $R_7$ and $R_6$ are independently lower alkyl. It is even more preferred that $R_7$ is the same as $R_6$. The most preferred values of $R_6$ and $R_7$ are methyl.

Besides protecting the carboxy and amido group on the main chain, the cyclopropyl methyl derivatives of the present invention can also protect the amino, amido, carboxy, mercapto and hydroxy groups on the side chain of the amino acid. For example, amino acids having a hydroxy group on the side chain include Ser, Thr, Tyr and the like, amino acids having an amino group on the side chain include Trp, Lys, Arg and His; amino acids having a mercapto group on the side chain include Cys and the like; amino acids having a carboxy group on the side chain include Asp and Glu, and the like, and amino acids having an amide functionality on the side chain include Gln and Asn and the like. The present invention encompasses amino acids of the Formula

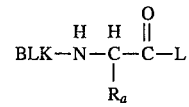

wherein BLK and L are as defined hereinabove and $R_a$ is a side chain of an α-amino acid having an amino or amide which is protected with a cyclopropyl derivative of the present invention, wherein the group

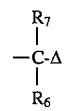

is attached to the nitrogen atom of the amine or amide. For example, the present invention includes protected amino acids of the formula

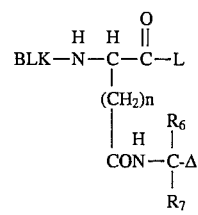

wherein L, $R_6$, $R_7$, BLK are defined hereinabove and n is 1–6, preferably 1 or 2. The preferred BLK, $R_6$ and $R_7$ groups are as defined hereinabove.

Furthermore, the present invention is directed to compounds of the formula

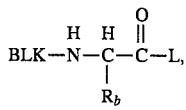

wherein BLK, L, are as defined hereinabove, and $R_b$ is a side chain of an α-amino acid, with the side chain having a mercapto, carboxy or hydroxy group and attached to the S-,

or O-atoms, respectively, in the side chain is a cyclopropylmethyl protecting group of the formula

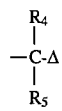

wherein $R_4$ and $R_5$ are as defined hereinabove. For example, the present invention includes protected amino acids of the formula

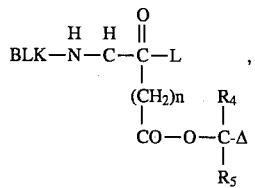

wherein BLK, L, $R_4$ and $R_5$ are as defined hereinabove, and n is 1–6, and preferably 1–2.

In all of the embodiments, the preferred value of BLK is BOC, FMOC, BSMOC, or CBZ.

A typical preparation of the peptide in accordance with the present invention involves the following steps 1) protection of the free carboxyl group in a first amino acid or a first peptide, unless the amino acid or peptide is anchored to a solid support. The free carboxyl group may be protected with a carboxy protecting group or a cyclopropylmethyl protecting group of the present invention.
2) protection of a functional group, e.g., carboxy, amido, amino, hydroxy or mercapto, with a cyclopropylmethyl protecting group of the present invention or one of the appropriate protecting groups enumerated hereinabove.
3) protection of the free amino group of a second amino acid or peptide.
4) coupling the first amino acid or peptide with the second amino acid or peptide.
5) removal of the protecting groups and the cyclopropylmethyl protecting groups in any order.

The procedure of steps 1–3 can be performed in any order.

Usually, the first amino acid or peptide is present in approximately equimolar amounts with the second amino acid or peptide, although the reaction can take place if the molar ratio of the former to the latter ranges from 1:3 to 3:1.

The coupling reaction described hereinabove can take place in the additional presence of a dehydrating agent such as DCC (dicyclohexylcarbodiimide) or EDC, (N-ethyl-N'-(3-dimethylaminopropyl)carbodiimide hydrochloride) and the like. The coupling reaction usually takes place in an inert organic solvent such as dimethylformamide (DMF) or ethers, such as ethyl ether, THF or dioxane. In fact DMF is the preferred solvent in the solid phase synthesis because of its favorable solvation properties. The reaction takes place under mild conditions usually ranging from about 0° to about 30° C. After the peptide is formed, the blocking groups are removed by techniques known to one skilled in the art.

The following sequence is illustrative of the coupling reaction; in the examples below, amino acids (AA) are used, although the procedure is general for amino acids and/or peptides:

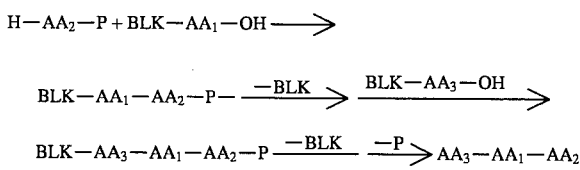

SCHEME I

In the above scheme, BLK is an amino acid blocking group, $AA_1$, $AA_2$ and $AA_3$ are first, second and third amino acid, respectively and P is a carboxy protecting group, such as benzyl, the cyclopropylmethyl protecting groups of the present invention, and the like.

As shown by the above scheme, the N-α amino protected amino acid is reacted with a second amino acid in which the carboxy group is protected.

A peptide is formed between the first amino acid and the second amino acid. The peptide chain can be increased by removing the alpha amino protecting group by techniques known to one skilled in the art and then reacting the corresponding dipeptide with another N-α amino protected amino acid in the presence of a compound of Formula I to form the corresponding tri-peptide. The N-α amino protecting group of the tri-peptide is removed and the above-cycle is repeated until the desired peptide has been obtained.

Prior to the coupling, a functional group on the amino acid or peptide, viz., carboxy, amino, mercapto, hydroxy or amido, is protected by a cyclopropylmethyl moiety of the present invention. Thus, at least one of the reactants in Scheme 1 has a cyclopropylmethyl protecting group. Furthermore, after the desired peptide has been obtained, this cyclopropylmethyl protecting group is removed. However, the various protecting group, including the cyclopropylmethyl protecting groups of the present invention, can be removed in any order.

The present invention can readily be utilized in solid phase peptide synthesis. Solid phase peptide synthesis is based on the stepwise assembly of a peptide chain while it is attached at one end to a solid support or solid phase peptide resin. Two methods are generally well known in the art.

One, the Merrifield method, employs a solid support for attachment of the amino acid or peptide residues. This method employs N-protected amino acids as building blocks which are added to an amino acid or peptide residue attached to the solid support at the acyl (acid) end of the molecule. After the peptide bond has been formed, the protecting group is removed and the cycle repeated. When a peptide having the desired sequence has been synthesized, it is then removed from the support.

The second method, the inverse Merrifield method, employs reagents attached to solid supports in a series of columns. The amino acid or peptide residue is passed through these columns in a series to form the desired amino acid sequence.

These Merrifield and inverse Merrifield methods are well known in the art and are discussed in U.S. Pat. Nos. 4,108,846, 3,839,396, 3,835,175, 4,508,657, 4,623,484, 4,575,541, 4,581,167, 4,394,519 as well as in *Advances in Enzymology*, 32, 221 (1969) and in PEPTIDES, Vol. 2, edited by Erhard Gross and Johannes Meienhoffer, Academic Press, New York pp. 3–255 (1980) and the contents thereof are incorporated by reference as if fully set forth herein.

In the above scheme, P may be a carboxy protecting group having the formula

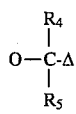

wherein $R_4$ and $R_5$ are defined herein. Regardless,

can be prepared by art recognized techniques. For example, when P has the value

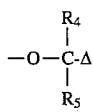

the protected amino acid, is reacted with a cyclopropylmethanol of the formula

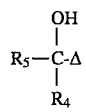

wherein $R_4$ and $R_5$ are as defined hereinabove under esterification conditions. The reaction is preferably performed in the presence of an acid catalyst, such as hydrochloric acid, p-toluenesulfonic acid, formic and trichloroacetic acid and the like. In addition, inasmuch as water is produced, the reaction is also preferably effected in the presence of a dehydrating agent or a molecular sieve to remove the water and drive the reaction to completion. Alternatively, the water can be removed by distillation or azeotropic distillation. As a result of the removal of the water, the cyclopropyl methyl containing ester is more readily formed.

Alternatively, the cyclopropyl methyl containing ester of the formula H—$AA_2$—P can be formed by first converting the amino acid to an acylating derivative, such as an acid halide, an ester such as a lower alkyl ester, an aryl ester, lower aralkyl ester or an anhydride. It is preferred that the amino acid be converted to the amino acid halide, especially chloride or fluoride. The amino acid halide is formed by reacting the amino acid with a halo generating reagent, such as thionyl chloride or cyanuric fluoride. The acylating derivative is then, in turn, reacted with the above-identified alcohol.

The present invention provides a method for converting an amino acid or the acylating derivative thereof to a protected amide, which in turn is reacted with another amino acid in accordance with the above scheme. When the polypeptide of desired length is formed, the cyclopropylmethyl protecting group is removed in order to generate the amide product.

An exemplary procedure for forming the protected amide is as follows.

The protected amide is formed by reacting the amino acid of the formula

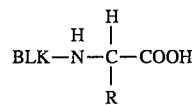

or acylating derivative thereof, e.g. the halide (Cl, F, etc.), with an amine of the formula

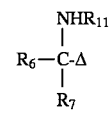

wherein $R_{11}$ is hydrogen or lower alkyl and $R_6$ and $R_7$ and BLK are as defined hereinabove.

The reaction is effected under amide forming conditions and preferably, for the acid, in the presence of a dehydration agent, such as those mentioned hereinabove. DCC is the most preferred.

The protected amide is then reacted with an amino acid, $AA_1$, in accordance with the above scheme until the polypeptide of sufficient length is formed. Then the cyclopropylmethyl protecting group is removed in accordance with the teachings hereinbelow, to form

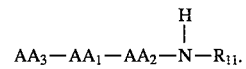

These examples illustrate the protection of a carboxy group or amide on the main chain. However, as indicated hereinabove, functional groups on the side chain may interfere with the coupling process, and as a result they need to be protected also. For instance, if the side chain contains a carboxy group, such as Glu or Asp, the carboxy group can be blocked using the cyclopropyl methyl derivatives of the present invention. The following scheme, exemplifies the procedure:

SCHEME 2

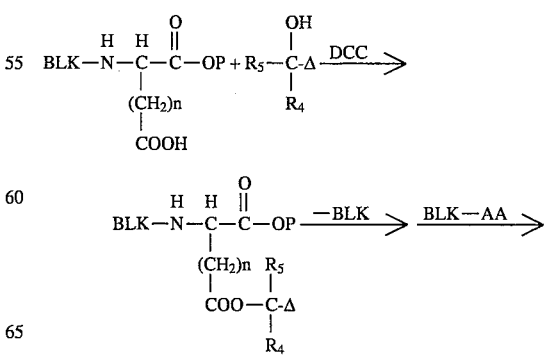

-continued
SCHEME 2

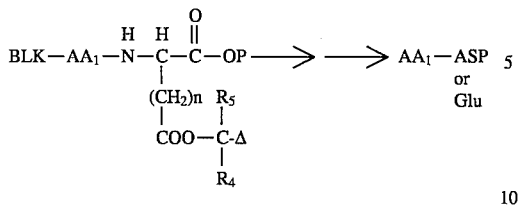

In the above scheme, P, BLK, AA$_1$, R$_4$ and R$_5$ are as defined hereinabove and n is 1 or 2. Here, the N-α-amino protected aspartic acid or glutamic acid is reacted with the cyclopropylmethanol under esterification conditions. The amino blocking group is removed and the resulting amino acid is reacted with a second N-α-amino blocked amino acid under peptide forming conditions to provide the dipeptide shown. Removal of the protecting groups affords the Asp
or
AA$_1$—Glu.

In the above scheme, if the desired product was

Asp—AA$_1$,
or
Glu then the P protecting group would have been removed from the Asp or Glu, and the resulting α-amino blocked aspartic acid or glutamic acid is reacted with AA$_2$—P$_1$, wherein P$_1$ is a carboxy protecting group. Removal of the protecting groups affords the Asp—AA$_1$.
or
Glu If the desired product in the above scheme contained Asn or Gln, rather than Asp or Glu, then the above scheme is followed, except that the amine of the formula

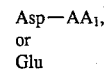

is substituted for the alcohol.

If the side chain of the amino acid contains a hydroxy group, such as Ser, Thr, Tyr, and the like, the process described in the above Scheme 2 is followed, except that the process for protecting the hydroxy group would be different. Using serine as an example and using CCl$_3$C≡N as the example for a nitrile, the following scheme is exemplary for protecting the hydroxy group.

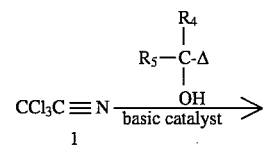

-continued

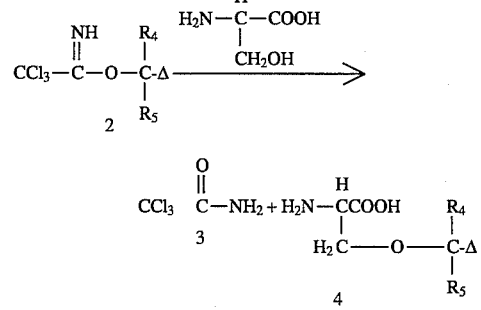

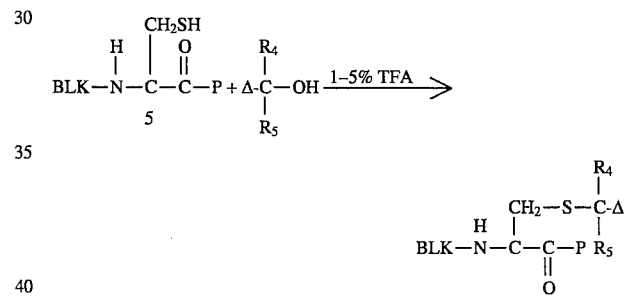

wherein BLK, R$_4$, R$_5$ are as defined hereinabove.

In the above scheme, the lower alkyl nitrile, which is preferably substituted with an election withdrawing group (1) is reacted with the alcohol in the presence of a base, such as sodium carbonate and the like to form the amino ester (2) which is then reacted with Ser to form the cyclopropylmethyl protected serine 4.

If the side chain has a mercapto group, such as cysteine, it can also be protected with the cyclopropylmethyl derivative described herein. For example, using cysteine as a representative example, the mercapto group can be protected as follows:

In the above reaction, BLK, R$_4$ and R$_5$ are defined herein above and P is a carboxy protecting group. In other words, the protected amino acid is reacted with the cyclopropylmethanol derivative in the presence of an acid under thioether formation conditions. The reaction is run in an inert solvent, such as methylene chloride, benzene and the like. An alternative procedure is to prepare the tosylate or mesylate of the alcohol by reacting the alcohol with tosyl chloride or mesylchloride, respectively, and, in turn, the resulting product is reacted with the mercapto compound, such as the protected system (5).

If the side chain has an amino functionality, such as histidine, it can also be protected with the cyclopropylmethyl derivative described hereinabove.

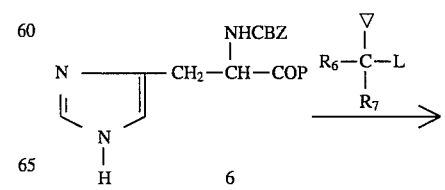

-continued

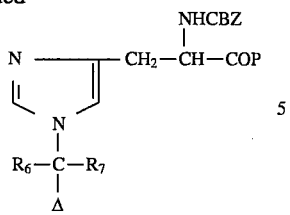

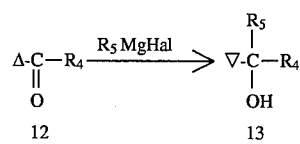

wherein R6, R$_7$, Cbz and P are as defined hereinabove and L is a good leaving group, such as tosylate or mesylate or halide, such as bromide or iodide.

In other words, the protected histidine compound (6) is reacted with the cyclopropylmethyl derivative under conditions effective to form the cyclopropylmethyl protected histidine. In this reaction it is preferred that the histidine (7) is present in excess.

In the case of arginine, the following scheme is exemplary for protecting the amino functionality:

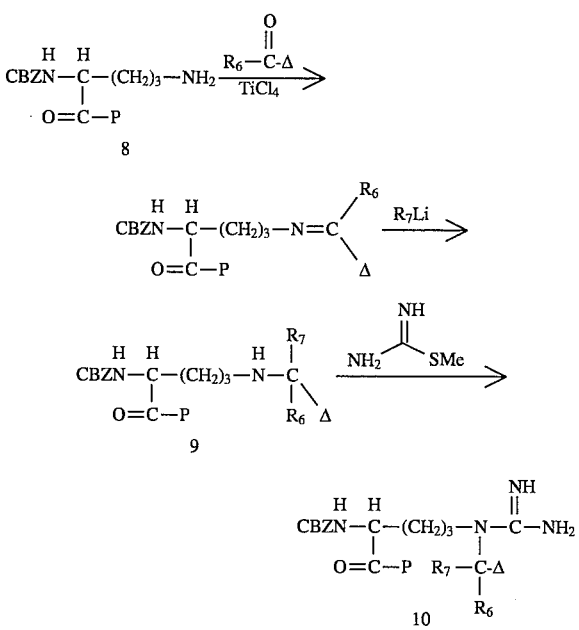

The amine 8 is reacted with a ketone and TiCl$_4$ followed by reaction with the organolithium compound, R$_7$Li, followed by reduction and reaction with 9 to form the cyclopropylmethyl protected arginine.

The cyclopropyl methanol derivative used in the above scheme is formed from art recognized techniques. An exemplary procedure is indicated hereinbelow.

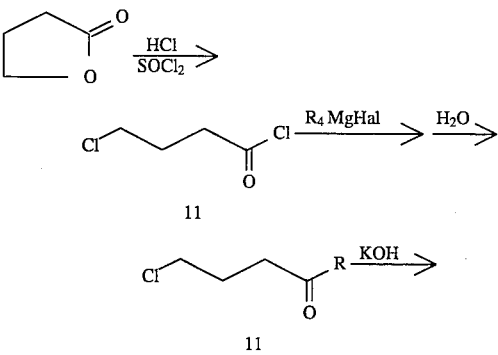

In other words, the lactone is cleaved with acid, such as hydrochloric acid and the like, and the resulting product is reacted with a halogenating agent, such as thionyl chloride. The resulting acid halide is reacted with a Grignard reagent to form the ketone. The resulting product is reacted with a strong base, such as KOH and the like to form 12. Without wishing to be bound, it is believed that the base abstracts the hydrogen from the ∝-carbon and promotes an intramolecular substitution reaction to form 12. 12 is then reacted in the presence of a Grignard reagent followed by water to form the cyclopropylmethanol derivative.

13 can be converted to the amine by reacting it with a sodium azide, in the presence of trichloracetic acid in an inert solvent, such as methylene chloride and the product thereof is reacted with lithium aluminum hydride followed by hydrochloric acid.

The cyclopropylmethyl protected amino acids are utilized to react with the amino acids or peptides in accordance with Scheme 1. When the peptide contains the desired amino acid residue, the various protecting groups are removed to form the desired polypeptide. The cyclopropyl methyl protecting groups of the present invention are removed under conditions effective to remove the protecting group without affecting the remainder of the product, since weakly acidic conditions are used. These weakly acidic conditions are strong enough to remove the protecting groups described hereinabove without affecting t-butyl based protecting groups for a period of about five hours. More specifically, weak acids such as 80% acetic acid, 1–2% CH$_3$SO$_3$H in methylene choride or acetic acid, or 1–2% p-toluenesulfonic acid in methylene chloride or acetic acid. 1–2% TFA in dichloromethane (DCM) or dilute acetic acid in hexafluoroisopropanol and the like can be used to remove the Cyclopropylmethyl protecting groups. It is preferred that the weak acid is 1–2% TFA in dichloromethane or dilute acetic acid, such as 1–10% HOAc and more preferably, 2–5% HOAc in hexafluoroisopropanol be utilized. For example, for the secondary cyclopropylmethyl protecting groups such as when R$_4$ is hydrogen and R$_5$ is cyclopropyl, dilute acetic acid in hexafluoroisopropanol (HFIP) or 1–2% TFA in methylene chlorine is sufficient for deblocking. These conditions do not affect typical t-butyl-derived blocking group. Furthermore, acid sensitive-tryptophan is unaffected by these conditions.

In the case of the tertiary cyclopropylmethyl derivatives, the blocking groups are even more sensitive to acids than the secondary cyclopropylmethyl groups if attached to oxygen, and therefore can be removed under the same or even milder acidic conditions. However, when used to protect nitrogen, they require more strongly acidic conditions. For example, conditions for removing the blocking groups from nitrogen are those which are used to remove t-butyl based protecting groups from the side chain. Thus, for example, 95% TFA is used for deblocking. Other acids that could be used include formic acid, liquid HF, 0.05N HBr in acetic acid, 5N HCl in THF and the like. There is no disadvantage since deblocking from nitrogen comes at the end of the synthesis and all side chain blocking groups such as t-butyl, are removed along with the nitrogen-fixed cyclopropylmethyl groups.

Please note that these acids described in the previous paragraph can be utilized to remove the tertiary cyclopropylmethyl groups, if attached to oxygen, and the secondary cyclopropylmethyl protecting group.

The following examples further illustrate the invention.

EXAMPLE 1

General Procedure for the preparation of FMOC-AA-ODCPM Esters. To a solution of 5 mmol of FMOC-AA-Cl in 20 mL of $CH_2Cl_2$ was added a mixture of 2 mL of (1:1) pyridine/dicyclopropyl methyl alcohol solution. The resulting solution was stirred at room temperature for 3 h, washed with phosphate buffer, pH 5.5 (20 mL×2), then saturated NaCl solution (20 mL×2). After drying over $MgSO_4$ and removal of solvent, the residue was crystallized from an appropriate solvent.

FMOC-Gly-ODCPM was recrystallized from EtOAc/hexane to give 1.38 g (71%) of white crystals, mp 118°–119° C.

Anal. Calcd. for $C_{24}H_{25}NO_4$:C,73.64:H,6.44; N,3.58. Found: C,73.54;H,6.44;N,3.54.

FMOC-Pro-ODCPM was crystallized from ether/hexane to give 1.5g (70%) of white crystals, mp 117°–118° C.

FMOC-Ala-ODCPM was crystallized from EtOAc/hexane to give 1.52 (75%) of white crystals, mp 115°–116° C.

Both FMOC-Val-ODCPM and FMOC-Ile-ODCPM were obtained as oils in yields of 80% and 82%, respectively.

EXAMPLE 2

Preparation of Dicyclopropylmethyl Amine Hydrochloride. To a solution of 4.48 g of dicyclopropylmethyl alcohol in 20 mL of $CH_2Cl_2$ was added 3.6 g of $NaN_3$ followed by 10 g of $CCl_3CO_2H$. The resulting mixture was stirred at room temperature for 3 h, diluted with 50 mL of $CH_2Cl_2$, washed with $NaHCO_3$ and NaCl solution. Drying over $MgSO_4$ and removal of solvent gave an oil (which was examined by high field $^1H$ NMR and shown to be contaminated by a small amount of ring-opening compound (less than 5%)) which was dissolved in a solution of 7 mL of toluene containing 2.5 g of hexadecyltributyl phosphonium bromide. To the solution was added 5 g of $NaBH_4$ in 15 mL of $H_2O$ through a dropping funnel over 30 min. The mixture was stirred at 80° C. for 16 h, layers separated and the organic layer extracted with 10% HCl. The pH of the aqueous solution was adjusted to 8–9 with NaOH and extracted with ether. After drying over $MgSO_4$, HCl gas was bubbled through the solution and the amine hydrochloride salt which had precipitated was collected by filtration and recrystallized from ether/MeOH to give 1.8 g (35%) of the salt as white crystals, mp 250° C. dec.

EXAMPLE 3

Preparation of Dicyclopropylamine-p-Toluene Sulfonic Acid Salt. To a stirred suspension of 0.81 g (0.021 mol) of $LiAlH_4$ in 150 ml of dry ether 1.69 g (0.0135 mol) of dimethylcyclopropylcarbinyl azide (dissolved in 10 ml of dry ether) was added dropwise. After the addition was complete, the solution was refluxed for 2 hours. In order to destroy the excess $LiAlH_4$ and any complex salts, commercial ether (10 ml) was added, followed by distilled water. The inorganic salts were filtered. The ether layer was separated, washed once with 20 ml of water and dried over $MgSO_4$ and 1.28 g (0.0046 mol, 0.5 eq.) of p-toluenesulfonic acid dissolved in 1 ml of MeOH was added dropwise. Stirring was continued for 15 minutes. The product was filtered. The same cycle of precipitation and collection of the product was made with 0.2 eq of TsOH. The collected white salt was recrystallized from MeOH/ether to give 2.34 g (60%) of the salt as white crystals, mp 168°–170° C.; IR (KBr) 3100, 1632, 1550 ($SO_2$) $cm^{-1}$; $^1H$ NMR ($CDCl_3$) δ0.3–0.6 (d, 4H, $CH_2CH_2$), 1.2 (s, 6H, 2×$(CH_3)_2CN$), 2.4 (s, 3H, $CH_3Ar$), 7.1–7.4 (d, 2H, aryl), 7.8–8.0 (bd, 3.3 H, aryl).

EXAMPLE 4

(ω)-Tritylasparagine: To a stirred suspension of 2 g (15.13 mmol) of asparagine, 7.89 g (30.3 mmol) of triphenylmethanol, and 2.9 ml (30.26 mmol) of acetic anhydride in 50 ml of glacial acid there was added 0.9 ml (17.5 mmol) of concentrated $H_2SO_4$. The reaction mixture was heated to 60° C. for 50 minutes and added in small portions to 25 ml of ice cold water. The pH was adjusted to 6 by added 10N NaOH. The mixture was kept at 0° C. for 4 hours. A white precipitate appeared and was filtered. After washing with water, toluene and Skelly F the solid was dried under vacuum to give 3.01 g (53.2%) of the protected amino acid as a white solid, mp 220° C. (dec.) lit mp>240° C.; $^1H$ NMR (DMSO-$d_6$) δ2.59 (m, 2H, $CHCH_2CO$), 3.0 (m, 2H, $NH_2$), 3.63 (m, 1H, NHCHCO), 7.2 (m, 16H, aryl+NH).

EXAMPLE 5

Preparation of FMOC-Phe-NHDCPM. To a solution of 610 mg (1.5 mmol) of FMOC-Phe-Cl in 15 mL of $CH_2Cl_2$ was added 237 mg (1.6 mmol) of the dicyclopropylmethyl amine hydrochloride followed by 15 mL of saturated $NaHCO_3$ solution. The resulting mixture was stirred at 0° C. for 30 min and then at room temperature for 30 min, the layers separated and washed with 5% HCl and saturated NaCl solution. After drying ($MgSO_4$) and removal of solvent, the residue was recrystallized (from MeOH/$H_2O$) to give 541 mg (75%) of the amide as a white solid, mp 211°–212° C. dec.

Anal. Calcd for $C_{31}H_{33}N_2O_3$: C,77.31; H,6.91; N,5.82. Found: C,77.28; H,6.81; N,5.78.

Deblocking Test: FMOC-Gly-ODCPM ester (20 mg, 0.051 mmol) was found to be deblocked by 1% TFA/$CH_2Cl_2$ solution immediately (less than 2 min). Both TLC and $^1H$ NMR results are in agreement. There was no difference in the rate of deblocking if $Et_3SiH$ was used as scavenger or not.

EXAMPLE 6

Preparation of BOC-Tyr(t-Bu)-Gly-OH. A solution of 390 mg (1 mmol) of FMOC-Gly-ODCPM ester in a 1:1 mixture of 20 mL ACN/$HNEt_2$ solution was stirred at room temperature for 40 min. After removal of solvent, the residue was dissolved in 5 mL of $CH_2Cl_2$ followed by addition of 1.2 mmol of crude BOC-Tyr(t-Bu)-F (generated from 450 mg (1.2 mmol) of BOC-Tyr(t-Bu)-OH and 8 mmole of cyanuric fluoride) in 5 mL of $CH_2Cl_2$ and 209 μL (1.2 mmol) of DIEA. The resulting mixture was stirred at room temperature for 15 min, 7.5. mL of TAEA was added and the mixture stirred for an additional 30 min, washed with saturated NaCl solution (20 mL×2), phosphate buffer pH 5.5 (20 mL×2) and 20 mL of saturated NaCl solution. After drying ($MgSO_4$) and removal of solvent, the residue was dissolved to 10 mL of hexafluoroisopropanol containing 2% of HOAc. The resulting solution was stirred at room temperature for 4 h, solvent evaporated, the residue dissolved in 20 mL of 5% $Na_2CO_3$ and extracted with ether. The aqueous solution was acidified with 10% citric acid to pH 2 and extracted with EtOAc. After drying ($MgSO_4$) and removal of solvent, the residue was crystallized from CHCl$_3$/Skelly B to give 197 mg (50%) of the dipeptide acid, mp 167°–169° C.

Anal. Calcd for C$_{20}$H$_{30}$N$_2$O$_6$: C,60.90;H,7.67; N,7.10. Found C,60.74;H,7.74;N,6.97.

EXAMPLE 7

Synthesis of Delta Sleep Inducing Peptide (DSIP), H-Trp-Ala-Gly-Gly-Asp-Ala-Ser-Gly-Glu-OH (SEQ ID NO:1).

(a) Synthesis of FMOC-Ser(t-Bu)-Gly-Glu-(OtBu)$_2$. Preparation of the title compound followed the standard 2-phase protocol, from 295 mg (1 mmol) of HCl.H-Glu-(OtBu)$_2$, with 1.2 eq of the FMOC-AA-F, 20 min for acylation and 30 min for deblocking using TAEA. The crude tripeptide was purified by column chromatography (30 g of silica gel) with elution by 400 mL of 20% acetone in Skelly B followed by 40% acetone in Skelly B to give 460 mg (67.5%) of the tripeptide after recrystallization from CHCl$_3$/Skelly B as a white solid, mp 121°–3° C.

Anal. Calcd. for C$_{37}$H$_{51}$N$_3$O$_9$: C,65.18; H,7.54; N,6.16. Found: C, 64.98; H, 7.53; N, 5.93.

(b) Synthesis of FMOC-Gly-Asp(OtBu)-Ala-ODCPM Ester. To a solution of 20 mL of 1:1 HNEt$_2$/ACN was added 405 mg (1 mmol) of FMOC-Ala-ODCPM ester. The resulting solution was stirred at room temperature for 40 min, solvent removed, the residue redissolved in 10 mL of methylenedichloride and the rest of the procedure followed the standard 2-phase protocol using 454 mg of FMOC-Asp(OtBu)-F and 329 mg of FMOC-Gly-F. The crude tripeptide ester was purified by column chromatography (40 g of silica gel) with elution by 400 mL of 20% of acetone in Skelly B followed by 45% of acetone in Skelly B to give, after recrystallization from EtOAc/Hexane, 420 mg (68%) of the pure tripeptide ester as a white solid, mp 152°–3° C.

Anal. Calcd for C$_{35}$H$_{43}$N$_3$O$_8$: C,66.33;H,6.84; N,6.63. Found: C,66.57;H,6.98;N,6.67.

Comment: When 4-AMP was used to replace TAEA the yield was comparable but formation of bulky precipitation during buffer extraction was observed.

(c) Synthesis of FMOC-Gly-Asp(OtBu)-Ala-OH. (1) To a solution of 5 mL of hexafluorisopropanol containing 100 µL of HOAc was added 100 mg of the above-mentioned tripeptide ester. The resulting solution was stirred at room temperature for 3 h. TLC showed 4 spots which include a trace of starting material and two other spots plus the major spot of the product. After solvent evaporation the residue was dissolved in 10 mL of 5% Na$_2$CO$_3$ solution and the aqueous solution extracted several times with ether. After acidification with 5% citric acid, the tripeptide acid was extracted with EtOAc solution, dried (MgSO$_4$) and solvent evaporated. After crystallization from CHCl$_3$/hexane there was obtained 50 mg (60%) of the pure tripeptide acid as a white solid, mp 166°–7° C.

(2) To a solution of 10 mL of 2% TFA in CH$_2$Cl$_2$ solution was added 120 mg of the tripeptide ester and the solution stirred at room temperature for 30 min. To the solution was added 2 mL of pyridine, the resulting solution evaporated under vacuum at room temperature, the residue dissolved in 20 mL of 5% Na$_2$CO$_3$ solution and extracted with 10 mL of EtOAc twice. After acidification with 5% citric acid, the tripeptide acid was extracted into EtOAc solution, dried (MgSO$_4$) and solvent removed to give a solid which was recrystallized from EtOAc/hexane to give 80 mg (78.6%) of the pure acid as a white solid, mp 166°–7° C.

(3) Treatment of 300 mg of the tripeptide ester with 15 mL of 2% TFA/CH$_2$Cl$_2$ containing 10 µL of HOAc at room temperature for 30 min gave, after recrystallization, 206 mg (81%) of the pure acid, mp 166°–7° C.

Anal. Calcd. for C$_{28}$H$_{33}$N$_3$O$_8$: C,62.32;H,6.16;N,7.79 Found: C, 61.84, H, 6.28, N, 7.50.

(d) Synthesis of BOC-Trp-Ala-Gly-ODCPM ester. To a mixture of 20 mL of 1:1 HNEt$_2$/ACN solution was added 391 mg (1 mmol) of FMOC-Gly-ODCPM ester and the resulting solution stirred at room temperature for 40 min, solvent removed and residue dissolved in 10 mL of CH$_2$Cl$_2$. To the solution was added 345 mg (1.1 eq) of FMOC-Ala-F and 191 µL (1.1 eq) of DIEA and the resulting solution was stirred at room temperature for 20 min, then 10 g of piperazine silica was added followed by 10 mL of CH$_3$CN. The slurry was sonicated for 2 h. TLC indicated deblocking and scavenging were incomplete and therefore 5 mL of HNEt$_2$ was added and deblocking was completed within 10 min. The piperazine silica was removed by filtration, washed thoroughly with CH$_3$CN and CH$_2$Cl$_2$. After evaporation, the residue was dissolved in 10 mL of CH$_2$Cl$_2$. To the solution was added 337 mg (1.1 eq) BOC-Trp-F and 191 µL (1.1 eq) of DIEA. The resulting solution was stirred at room temperature for 20 min, washed with 5% Na$_2$CO$_3$, 5% citric acid and saturated NaCl solution. After drying over MgSO$_4$ and solvent removal, the residue was purified by column chromatography (40 g of silica) with elution by 350 mL of 20% of acetone in Skelly B followed by 40% of acetone in Skelly B to give 270 mg (51.3%) of the tripeptide ester as a white solid, mp 95°–97° C.

Anal. Calcd for C$_{28}$H$_{38}$N$_4$O$_6$:C,63.86;H,7.27; N,10.64. Found: C,63.66;H,7.33;N,10.37.

(e) Synthesis of BOC-Trp-Ala-Gly-OH. To a solution of 200 mg of the above-mentioned tripeptide in 20 mL of hexafluoro 2-propanol was added 200 µL of thioanisole and 100 µL of formic acid. The resulting solution was stirred at room temperature for 25 min when TLC showed no more starting materials. 2 mL of pyridine was added and the solvent evaporated. The residue was dissolved in 5% Na$_2$CO$_3$ solution and extracted with 30 mL of EtOAc. The aqueous solution was acidified with 5% citric solution to pH 2, extracted with 50 mL of EtOAc and the organic solution washed with saturated NaCl solution. After drying and solvent removal there was obtained a residue which was crystallized from EtOAc/hexane to give 120 mg (73.1%) of the tripeptide acid as a white solid, mp 215° C. dec. In addition to the desired product there was isolated 10 mg of an unidentified impurity.

(f) Synthesis of FMOC-Gly-Asp(OtBu)-Ala-Ser(tBu)-Gly-Glu(OtBu)$_2$(SEQ ID NO:2). To a mixture of 10 mL of 1:1 HNEt$_2$/ACN solution was added 204 mg of FMOC-Ser(tBu)-Gly-Glu(OtBu)$_2$ and the resulting solution stirred at room temperature for 1 h, solvent removed and the residue dissolved in 3 mL of DMF. To the solution was added 183.05 mg of FMOC-Gly-Asp(OtBu)-Ala-OH, 160 mg of BOP reagent, 54 mg of HOBt and 61 µL of DIEA. The resulting solution was stirred at 0° C. overnight and at room temperature for 4 h, solvent removed with the aid of a vacuum pump, and the residue washed thoroughly with MeOH and recrystallized from THF to give 150 mg (52%) of the protected hexapeptide as a white solid, mp 187°–193° C.

(g) Synthesis of BOC-Trp-Ala-Gly-Gly-Asp(OtBu)-Ala-Ser(tBu)-Gly-Glu(OtBu)$_2$(SEQ ID NO:3). A suspension of 96.8 mg (0.1 mmol) of the FMOC-hexapeptide in 4 mL of 1:1 NEt$_2$NH/ACN solution was stirred at room temperature for 50 min (TLC) and the solvent removed with the aid of a vacuum pump to give a white solid which was dissolved in 3 mL of dry DMF. To the solution was added 64.8 mg (1.5 eq) of BOC-Trp-Ala-Gly-OH, 88.4 mg (2 eq) of BOP reagent, 30.6 mg (2 eq) of HOBt and 34.8 µL (2 eq) of DIEA. The resulting solution was stirred at room temperature for 14 h and the solvent removed to give a residue which was washed thoroughly with MeOH and ether to give 30 mg of the protected nonapeptide as a white solid.

(h) Treatment of the protected peptide with TFA/H$_2$O ethane-1,2-dithiol (95/4/1) gave the fully deblocked delta sleep inducing peptide as the TFA salt.

EXAMPLE 8

Synthesis of Z-Asn(DCPM)-OBzl. To a solution of 1.57 g (4.4 mmol) of Z-Asp-OBzl in 35 mL of 5:1 ACN/DMF solution was added 660 mg (4.45 mmol) of dicyclopropylmethylamine hydrochloride, 2.14 g (4.84 mmol) of BOP reagent and 1.53 mL (8.8 mmol) of DIEA. The resulting solution was stirred at room temperature overnight, solvent removed, the residue dissolved in 100 mL of EtOAc and the solution washed with 5% HCl, saturated NaHCO$_3$ and saturated NaCl solution. After drying (MgSO$_4$) and removal of solvent, there was obtained a white solid which was recrystallized from EtOAc/Skelly B to give 1.67 g (84.1%) of the amide as a white solid, mp 210° C.

EXAMPLE 9

Synthesis of FMOC-Asn(DCMP)-OH. To a solution of 1.27 g (2.82 mmol) of Z-Asn(DCPM)-OBzl in 100 mL of 9:1 EtOH/DMF solution in a pressure bottle was added 450 mg of 5% Pd-C and the pressure charged to 50 psi. After shaking for 3 days, there was obtained 470 mg of the side-chain protected asparagine as a grayish solid which was dissolved in 35 mL of saturated NaHCO$_3$ solution. To the solution was added 807 mg of FMOC-OSu in 35 mL of dioxane. The resulting mixture was stirred at room temperature overnight, extracted with ether, acidified with 5% HCl and the product which had precipitated was collected by filtration and washed well with ether and air dried to give 680 mg (72.9%) of the protected amino acid as a white solid, mp 173°–4° C.

Anal. Calcd for C$_{26}$H$_{28}$N$_2$O$_5$: C,69.63;H,6.29; N,6.25. Found: C,69.42;H,6.54;N,6.19.

EXAMPLE 10

Synthesis of FMOC-Asn-Trp-OMe. To a solution of 354 mg (1 mmol) of FMOC-Asn-OH, 153 mg (1 mmol) of HOBt in 5 mL of DMF was added a solution of 1 mmol of proton sponge and 254 mg (1 mmol) of HCl.H-Trp-OMe in 5 mL of DMF. To the mixture cooled in an ice-bath was added 227 mg (1.1 mmol) of DCC. The resulting mixture was kept in a freezer for 3 h and then stirred at room temperature overnight. After aqueous work-up, the residue was crystallized from EtOH to give 301 mg (56%) of the dipeptide as a white solid, mp 185° C. dec.

Anal. Calcd for C$_{31}$H$_{30}$N$_4$O$_5$: C,67.14;H,5.45; N,10.10. Found: C,67.00;H,5.54;N,10.08.

EXAMPLE 11

Synthesis of FMOC-Asn(DCPM)-Trp-OMe. To a solution of 224 mg (0.5 mmol) of FMOC-Asn(DCPM)-OH, 140 mg (0.55 mmol) of HCl.H-Trp-OMe, 80 mg (0.52 mmol) of HOBt, and 240 mg (0.55 mmol) of BOP reagent in a mixture of 10 mL of 1:1 ACN/DMF solution was added 191 µL (1.1 mmol) of DIEA. The resulting mixture was kept in a freezer for 3 h, and then stirred at room temperature overnight. After removal of solvent, the residue was washed successively with MeOH and ether and finally recrystallized from EtOH/Skelly B in the presence of a few drops of THF to give 337 mg (52%) of the dipeptide as a white solid, mp 221° C. dec.

Anal. Calcd for C$_{38}$H$_{40}$N$_4$O$_6$: C,70.35;H,6.21; N,8.64. Found: C,70.29;H,6.45;N,8.54.

Comment: This dipeptide is very insoluble in most organic solvents. Washing with MeOH and ether seems to be effective to get rid of any impurities but only a low yield of final product is obtained.

EXAMPLE 12

Synthesis of FMOC-Asn(DOD)-Trp-OMe. This compound was prepared in the same manner as described directly above from 580 mg (1 mmol) of FMOC-Asn(Dod)-OH. After washing, there was obtained 585 mg (75%) of the ester as a white solid, mp 224° C. dec.

Anal. Calcd for C$_{46}$H$_{44}$N$_4$O$_8$: C,70.75;H,5.68;N,7.17. Found: C,70.64;H,5.88;N,7.17.

Comment: This compound is also very insoluble.

Deblocking Test: Deblocking of 10 mg of FMOC-Asn-(DOD)-Trp-OMe in 1 mL of TFA solution took 2½ h but TLC showed that only little of the product was formed. Under the same conditions deblocking of FMOC-Asn(D-CPM)-Trp-OMe took 4–5 h. TLC analysis showed the reaction mixture to be slightly cleaner than that from FMOC-Asn(DOD)-Trp-OMe. FMOC-Asn-Trp-OMe was found to be unstable in TFA solution.

EXAMPLE 13

Preparation of Dimethylcyclopropyl Carbinol. The preparation followed the reported method from 31 g of cyclopropyl methyl ketone, 60 g of MeI and 9.6 of Mg turnings in 150 mL of anhydrous ether. After distillation, the fraction boiling at 123°–5° C. was collected to give 25 g (67%) of the tertiary alcohol as a colorless liquid.

EXAMPLE 14

Preparation of Dimethylcyclopropylmethyl Azide. A solution of 5 g (50 mmol) of the alcohol, 4.5 of NaN$_3$ and 12.5 g of trichloroacetic acid in 50 mL of CHCl$_3$ was stirred at room temperature for 1–2 h, diluted with 150 mL of ether, washed thoroughly with 5% NaHCO$_3$ solution and saturated NaCl solution. After drying over MgSO$_4$ and solvent removal there was obtained 6.24 of the azide as a liquid (quantitative).

Comment: Without dilution by ether the impurity could not be removed by aqueous work-up. The impurity peak can be clearly seen by IR (extra peak at 1760 cm$^{-1}$). When CH$_2$Cl$_2$ was used as solvent, ring-opening was observed. On the contrary reaction did not take place in either CCl$_4$ or 1:1 CH$_2$Cl$_2$/CCl$_4$ solution.

EXAMPLE 15

Preparation of Dimethylcyclopropylmethyl Amine Hydrochloride. To a solution of 1.8 g of the azido compound and 2.5 g of hexadecyltributyl phosphonium bromide in 7 mL of toluene was added a solution of 5 g of NaBH$_4$ in 15 mL of water dropwise over 30 min at 80° C. the resulting solution was kept at this temperature with stirring for 72 h, allowed to cool to room temperature, and extracted with 10 mL of toluene. The combined organic solution was washed with 10% HCl (15 mL×2), the pH of the aqueous solution then adjusted to 8–9 with NaOH and the solution extracted with ether. After layer separation, the ether solution was washed with saturated NaCl solution, dried, and HCl gas passed through. The precipitated amine salt was collected by filtration, washed with ether and dried under vacuum. After recrystallization from MeOH/ether there was obtained 720 mg (36.8%) of the salt as white crystals, mp 235° C. dec, lit. 223°–225° C.

Comment: Attempted hydrogenolysis using Pd/C or Lindlar catalyst did not work. Similarly the Staudinger reaction ($Ph_3P/H_2O/THF$) did not work.

EXAMPLE 16

Preparation of FMOC-Phe-NHDMCPM. To a solution of 389 mg (1 mmol) of FMOC-Phe-F and 163 mg (1.2 mmol) of the amine salt in 10 mL of $CH_2Cl_2$ was added 400 µL (2.3 mmol) of DIEA. The resulting solution was stirred for 30 min, washed with 5% $Na_2CO_3$, 5% HCl and NaCl solution. After drying over $MgSO_4$ and removal of solvent, the residue was purified by column chromatography (40 g of silica) with elution by 30% acetone in Skelly B to give, after recrystallization from ether/hexane, 300 mg (67.8%) of the amide as a white solid, mp 124°–5° C.

Anal. Calcd for $C_{30}H_{32}N_2O_3$: C,76.90;H,6.88; N,5.98. Found: C,77.07;H,6.95;N,5.99.

EXAMPLE 17

Preparation of CBZ-Asn(DMCPM)-OBzl. To a solution of 820 mg (2.3 mmol) of CBZ-Asp-OBzl, 470 mg (1.5 eq) of the amine hydrochloride, and 1.53 g (1.5 eq) of BOP reagent in 10 mL of ACN was added 1.2 mL (3 eq) of DIEA. The resulting solution was stirred at room temperature overnight, solvent evaporated, the residue dissolved in 20 mL of EtOAc and the solution washed with 5% HCl, 5% $Na_2CO_3$ and saturated NaCl solution. After drying over $MgSO_4$ and removal of solvent there was obtained a solid which was recrystallized from $CHCl_3$/Skelly B to give the protected amide as white crystals, mp 84°–5° C.

Anal.Calcd for $C_{25}H_{30}N_2O_5$: C,68.47;H,6.90; N,6.39. Found: C,68.48;H,7.01;N,6.39.

EXAMPLE 18

Preparation of FMOC-Asn(DMCPM)-OH. To a solution of 700 mg (1.6 mmol) of CBZ-Asn(DMCPM)-OBzl in 50 mL of EtOH was added 200 mg of 5% Pd-C in a pressure bottle and the pressure was charged to 50 psi. After shaking overnight, the pressure was released, the catalyst removed and solvent evaporated to give a greenish-grey solid which was dissolved in 35 mL of 10% $NaHCO_3$ solution. To the solution was added 650 mg (1.2 eq) of FMOC-OSu in 35 mL of dioxane slowly. The resulting solution was stirred at room temperature overnight, extracted with ether (50 mL×2), acidified with 5% HCl to pH 2 and extracted with EtOAc (20 mL×2). After drying ($MgSO_4$) and removal of solvent, the residue was purified by column chromatography (40 g of silica) with elution by 5–10% MeOH in $CHCl_3$ containing 1% HOAc. After recrystallization from EtOAc/Skelly B there was obtained 400 mg (59%) of the acid as a white solid, mp 163° C.

EXAMPLE 19

Synthesis of FMOC-Asn(DMCPM)-Trp-OMe. To a solution of 200 mg (0.47 mmol) of FMOC-Asn(DMCPM)-OH, 120 mg (1 eq) of HCl.H-Trp-OMe and 250 mg (1.2 eq) of BOP reagent in 5 mL of ACN was added 172 µL (2.1 eq) of DIEA. The resulting solution was stirred at room temperature overnight, solvent evaporated, the residue dissolved in 15 mL of EtOAc and washed with 5% HCl, 5% $Na_2CO_3$ and saturated NaCl solution. After drying over $MgSO_4$ and removal of solvent the residue was purified by column chromatography (20 g of silica) with elution by 50% acetone in Skelly B to give 220 mg (75%) of the dipeptide ester, mp 100° C. dec.

Anal. Calcd for $C_{36}H_{40}N_4O_6$: C,69.21;H,6.45; N,8.97. Found: C,69.39;H,6.48;N,8.80.

Deblocking Test: A solution of 10 mg of FMOC-Asn(DMCPM)-Trp-OMe in 1 mL of TFA was monitored by TLC. After 30 min most starting material disappeared and a by-product started to form. After 1 h deblocking was completed. A solution of 25 mg of FMOC-Phe-NHDMCPM in 95% TFA was stirred for 30 min, diluted with $H_2O$ and the product which had precipitated collected by filtration. After washing with water and drying under vacuum there was obtained 20 mg (96%) of FMOC-Phe-$NH_2$. NMR and IR confirmed the structure.

The above preferred embodiments and examples are given to illustrate the scope and spirit of the present invention. These embodiments and examples will make apparent to those skilled in the art other embodiments and examples. These other embodiments are also examples within the contemplation of the present invention. Therefore, the present invention should be limited only by the appended claims.

---

What is claimed is:

1. A compound of the formula:

$$\text{BLK}-\underset{|}{\overset{H}{N}}-\underset{\underset{R}{|}}{\overset{H}{C}}-\overset{O}{\underset{\|}{C}}-X$$

wherein R is one of the side chains of a naturally occurring amino acid;

Blk is a base labile N α-amino acid protecting group, a protecting group removed by acid, a protecting group removed by reduction or catalytic hydrogenation, a protecting group removed by a nucleophile or formyl, acetyl, or trifluoroacetyl; and X is $OR_2$ or $NR_3^{R_9}$;

$R_2$ is $-\underset{\underset{R_5}{|}}{\overset{\overset{R_4}{|}}{C}}-\Delta$;

$R_3$ is $-\underset{\underset{R_6}{|}}{\overset{\overset{R_7}{|}}{C}}-\Delta$;

$R_4$ is hydrogen or lower alkyl;

$R_7$ and $R_5$ are independently lower alkyl, aryl, aryl lower alkyl, cycloloweralkyl or cycloloweralkyl lower alkyl;

$R_6$ is lower alkyl, aryl lower alkyl, or aryl; and $R_9$ is H or lower alkyl.

2. The coumpound according to claim 1 wherein X is $OR_2$.

3. The compound according to claim 2 wherein

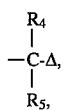

wherein $R_4$ is hydrogen and $R_5$ is lower alkyl, cyclolower-alkyl, aryl, aryl lower alkyl, or lower cycloalkyl lower alkyl.

4. The compound according to claim 3 wherein $R_5$ is cylcoloweralkyl or aryl.

5. The compound according to claim 4 wherein $R_5$ is cyclopropyl or phenyl.

6. The compound according to claim 5 wherein $R_5$ is cyclopropyl.

7. The compound according to claim 1 wherein X is

8. The compound according to claim 7 wherein $R_3$ is

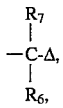

wherein $R_6$ is lower alkyl and $R_7$ is lower alkyl, aryl, aryl cylcoloweralkyl, cycloloweralkyl or lower cylcoalkyl lower alkyl.

9. The compound according to claim 8 wherein $R_7$ is lower alkyl and $R_6$ is lower alkyl.

10. The compound according to claim 9 wherein $R_7$ is the same as $R_6$.

11. The compound according to claim 9 wherein $R_6$ and $R_7$ are methyl.

12. A compound of the formula

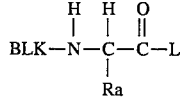

wherein BLK is an amino protecting group;

L is halide, OH or $OR_8$;

$R_a$ is a side chain of a naturally occurring amino acid having a primary or secondary amino or amido and attached to the nitrogen atom at said amino or amido group is a moiety of the formula:

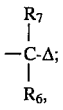

wherein $R_6$ is lower alkyl, aryl lower alkyl or aryl;

$R_7$ is lower alkyl, aryl lower alkyl, aryl, lower cycloalkyl or lower cycloalkyl lower alkyl; and $R_8$ is hydrogen or lower alkyl.

13. The compound according to claim 12 wherein $R_6$ is lower alkyl.

14. The compound according to claim 12 wherein $R_6$ is lower alkyl and $R_7$ is lower alkyl.

15. The compound according to claim 14 wherein $R_6$ is the same as $R_7$.

16. The compound according to claim 15 wherein $R_6$ and $R_7$ are methyl.

17. The compound according to claim 12 wherein the naturally occurring amino acid is asparagine, glutamine, lysine, arginine, or histidine.

18. The compound according to claim 12 wherein L is a halide.

19. The compound according to claim 12 wherein L is chloride.

20. The compound according to claim 12 wherein L is fluoride.

21. A compound of the formula:

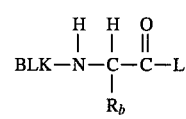

wherein BLK is a base labile N α-amino acid a protecting group, a protecting group removed by acid, a protecting group removed by reduction of catalytic hydrogenation, protecting group removed by nucleophile or formyl, acetyl, or trifluoroacetyl;

L is halide or $OR_8$;

$R_b$ is a side chain of a naturally occurring amino acid, said side chain containing a carboxy group, mercapto group or hydroxy group, and attached to said carboxy, mercapto or hydroxy is a moiety of the formula:

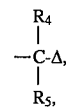

wherein $R_4$ is hydrogen or lower alkyl;

$R_5$ is lower alkyl, aryl, aryl lower alkyl, lower cycloalkyl or lower cycloalkyl lower alkyl; and $R_8$ is hydrogen or lower alkyl.

22. The compound according to claim 21 wherein $R_4$ is hydrogen.

23. The compound according to claim 21 wherein $R_4$ is hydrogen and $R_5$ is lower cycloalkyl.

24. The compound according to claim 21 wherein $R_5$ is lower cycloalkyl or aryl.

25. The compound according to claim 24 wherein $R_5$ is lower cycloalkyl.

26. The compound according to claim 25 wherein $R_5$ is cyclopropyl.

27. The compound according to claim 21 wherein the amino acid is cysteine, tyrosine, serine, threonine, aspartic acid or glutamic acid.

28. The compound according to claim 21 wherein L is halide.

29. The compound according to claim 28 wherein L is fluoride.

30. An amino acid moiety of the formula:

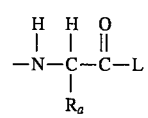

wherein $R_a$ is a side chain of a naturally occurring amino acid having a primary or secondary amine or a primary or secondary amide, and attached to said nitrogen atom of said amine or amide group is a moiety of the formula:

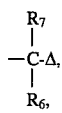

wherein

L is $OR_8$ or halide;

$R_6$ is lower alkyl, aryl, or aryl lower alkyl;

$R_7$ is lower alkyl, aryl, aryl lower alkyl, lower cycloalkyl or lower cycloalkyl lower alkyl; and $R_8$ is lower alkyl or hydrogen.

31. The amino acid moiety of claim 30 wherein $R_6$ and $R_7$ are independently lower alkyl.

32. The amino acid moiety of claim 30 wherein $R_6$ is the same as $R_7$.

33. The amino acid moiety of claim 32 wherein $R_6$ and $R_7$ are methyl.

34. The amino acid moiety according to claim 30 wherein the amino acid is arginine, glutamine, lysine, or histidine.

35. A method for protecting a carboxy group of an organic molecule during a reaction which modifies a portion of the molecule other than the protected carboxy group comprising (a) reacting the carboxy group or an acylating derivative thereof with a compound of the formula:

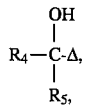

under esterification conditions to form a protected carboxy group, wherein $R_5$ is lower alkyl, aryl, lower arylalkyl, lower cycloalkyl or lower cycloalkyl lower alkyl; and $R_4$ is hydrogen or $R_5$;

(b) modifying a portion of the molecule other than the protected carboxy group by chemical reaction; and (c) removing the protecting group from the carboxy group.

36. The method of claim 35 wherein the acylating derivative is an acid halide, wherein the halide is F, Cl, Br, or I.

37. The method of claim 36 wherein the acid halide is a carboxylic acid fluoride or carboxylic acid chloride.

38. The method of claim 35 wherein the acylating derivative of the carboxylic acid is a carboxylic acid ester, wherein the ester is a lower alkanoate, lower cycloalkanoate or aryloate.

39. The method of claim 35 wherein $R_4$ is hydrogen and $R_5$ is cyclopropyl.

40. A method of protecting a carboxy group during peptide formation between a first amino acid or peptide having a free amino and carboxy group and a second amino acid or peptide having a free carboxy group and an Nα-protected amino group comprising (a) esterifying the carboxy group of the first amino acid, or peptide with a cyclopropylmethanol of the formula:

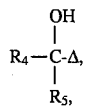

wherein $R_4$ is hydrogen or lower alkyl; and $R_5$ is lower alkyl, aryl, aryl lower alkyl, lower cycloalkyl, or lower cycloalkyl lower alkyl to form a cyclopropylmethylester protecting group;

(b) reacting the product of (a) with said second amino acid or peptide; and (c) removing the cyclopropylmethyl ester protecting group.

41. The method according to claim 40 wherein $R_4$ is hydrogen.

42. The method according to claim 41 wherein $R_5$ is lower alkyl, aryl or lower cycloalkyl.

43. The method according to claim 40 wherein $R_4$ is hydrogen and $R_5$ is lower alkyl, lower cycloalkyl or aryl.

44. The method according to claim 40 wherein $R_5$ is lower cycloalkyl or aryl.

45. The method according to claim 44 wherein $R_5$ is phenyl or cyclopropyl.

46. The method according to claim 43 wherein $R_5$ is phenyl or cyclopropyl.

47. The method according to claim 40 wherein the cyclopropylmethyl ester protecting group is removed by acid hydrolysis.

48. The method according to claim 47 wherein the cyclopropylmethyl ester protecting group is removed by reacting the product of (b) with dilute trifluoracetic acid or with dilute acetic acid.

49. In the synthesis of a peptide wherein a first amino acid or peptide having free amino and carboxy groups is coupled via a peptide linkage to the carboxyl group of a second N α-amino protected amino acid or peptide and the cycle repeated until the desired peptide has been obtained, the improvement comprising protecting the carboxy group of the first amino acid by (a) esterifying the first amino acid with a cyclopropylmethanol of the formula:

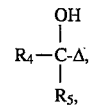

to provide a carboxy group protected as a cyclopropylmethyl ester, wherein $R_4$ is hydrogen or lower alkyl; and $R_5$ is lower alkyl, aryl, aryl lower alkyl, lower cycloalkyl, or lower cycloalkyl lower alkyl; and (b) when the desired peptide is obtained, removing said cyclopropylmethyl ester protecting group with acid hydrolysis.

50. The improved process according to claim 49 wherein the protecting group is removed by reacting the product of (a) with dilute trifluoroacetic acid or dilute acetic acid.

51. The improved process according to claim 49 wherein $R_4$ is hydrogen.

52. The improved process according to claim 49 wherein $R_5$ is aryl or a lower cycloalkyl.

53. The improved process according to claim 49 wherein $R_5$ is aryl or lower cycloalkyl and $R_4$ is hydrogen.

54. The improved process according to claim 52 wherein $R_5$ is phenyl or cyclopropyl.

55. The improved process according to claim 53 wherein $R_5$ is phenyl or cyclopropyl.

56. In the synthesis of a peptide wherein a first amino acid or peptide having a free carboxy group on the side chain thereof is coupled via a peptide linkage to the carboxyl group of a second N α-amino protected amino acid or peptide and the cycle repeated until the desired peptide has been obtained, the improvement comprising protecting the carboxy group on the side chain by esterifying it with a cyclopropylmethanol of the formula:

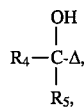

to provide a carboxy group having a cyclopropylmethyl protecting group bonded thereto,
wherein $R_4$ is hydrogen or lower alkyl;

$R_5$ is lower alkyl, aryl, aryl lower alkyl, lower cycloalkyl or lower cycloalkyl lower alkyl; and (b) after the desired peptide is obtained, removing said cyclopropylmethyl protecting group with acid hydrolysis.

57. The improved process according to claim 56 wherein the first amino acid or peptide contains Glu or Asp.

58. The improved process according to claim 56 wherein $R_4$ is hydrogen.

59. The improved process according to claim 56 wherein $R_5$ is aryl or lower cycloalkyl.

60. The improved process according to claim 56 wherein $R_4$ is hydrogen and $R_5$ is aryl or lower cycloalkyl.

61. The improved process according to claim 60 wherein $R_4$ is hydrogen and $R_5$ is phenyl or cyclopropyl.

62. In the synthesis of a peptide wherein a first amino acid or peptide having a free amino group and a free carboxy group or acylating derivative of said carboxy group is coupled via a peptide linkage to the carboxy group of a second N α-amino protected amino acid or peptide derivative, and the cycle repeated until the desired peptide has been obtained, the improvement comprising reacting the carboxy group or acylating derivative of the carboxy group on the first amino acid or peptide with a cyclopropylmethylamine of the formula:

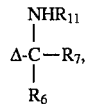

under amide forming conditions to provide an amide protected with a cyclopropylmethyl protecting group, wherein $R_7$ and $R_6$ independently are lower alkyl, lower cycloalkyl, lower cycloalkyl lower alkyl, aryl or aryl lower alkyl; and $R_{11}$ is hydrogen or lower alkyl; and (b) after the desired peptide is obtained, removing said cyclopropylmethyl protecting group, thereby converting the free carboxy group of the first amino acid or peptide to an amide.

63. The improved process according to claim 62 wherein $R_6$ and $R_7$ are independently lower alkyl.

64. The improved process according to claim 62 wherein $R_6$ and $R_7$ are the same.

65. The improved process according to claim 62 wherein $R_6$ and $R_7$ are methyl.

66. The improved process according to claim 62 wherein $R_{11}$ is hydrogen.

67. The improved process according to claim 62 wherein the protecting group is removed by acid hydrolysis.

68. The improved process according to claim 67 wherein the protecting group is removed by 95% trifluoracetic acid.

69. A process for converting a carboxy group on an organic molecule to an amide and protecting the amide during a reaction which modifies a portion of the molecule other than the protected amide comprising:

(a) reacting the carboxy group or an acylating derivative thereof with a compound of the formula:

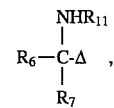

under amide forming conditions; thereby forming a cyclopropylmethyl protected amide, wherein $R_6$ and $R_7$ are independently lower alkyl, aryl, aryl lower alkyl, lower cycloalkyl, or cycloalkyl lower alkyl;

and $R_{11}$ is hydrogen or lower alkyl, (b) modifying a portion of the molecule other than the protected amide by chemical reaction, and (c) removing the protecting group from the amide.

70. The process of claim 69 wherein the acylating derivative is an acid halide, wherein the halide is F, Cl, Br or I.

71. The process of claim 70 wherein the acid halide is a carboxylic acid fluoride or carboxylic acid chloride.

72. The process of claim 69 wherein the cyclopropylmethyl protecting group is removed by acid hydrolysis.

73. The process of claim 72 wherein the acid is 95% TFA.

74. The process according to claim 69 wherein $R_{11}$ is hydrogen.

75. The process according to claim 69 wherein $R_6$ and $R_7$ are independently lower alkyl.

76. The process according to claim 69 wherein $R_6$ and $R_7$ are the same.

77. The process according to claim 69 wherein $R_6$ and $R_7$ are methyl.

78. The process for converting a carboxy group on the side chain of an amino acid or peptide to an amide and protecting the amide during peptide synthesis which comprises (a) reacting the carboxy group on the side chain of a first amino acid or peptide with a cyclopropylmethylamine of the formula:

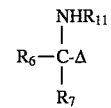

under amide forming conditions to form the cyclopropylmethyl protected amide;

(b) reacting the product of (a) with a second amino acid or peptide under peptide forming conditions; and (c) removing the cyclopropylmethyl group from the side chain.

79. The process according to claim 78 wherein the first amino acid is Glu or Asp.

80. The process according to claim 78 wherein the first peptide is a peptide containing Glu or Asp.

81. In a process for protecting the mercapto group on a cysteine during peptide synthesis wherein a first compound selected from the group consisting of an amino acid and peptide is coupled via a peptide linkage to the carboxyl group of a second compound selected from the group consisting of a second amino acid and second peptide and the cycle repeated until the desired peptide has been obtained and wherein the first compound contains a cysteine, the improvement comprising reacting the first compound with a cyclopropylmethanol of the formula:

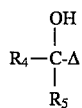

under thioether forming conditions to form a cyclopropylmethyl protected thiol prior to the coupling step wherein $R_4$ is hydrogen or lower alkyl; and $R_5$ is lower alkyl, lower cycloalkyl, aryl, aryl lower alkyl or lower cycloalkyl; and (b) after the desired peptide is obtained, removing the cyclopropylmethyl protecting group by acid hydrolysis.

82. The improved process according to claim 81 wherein $R_4$ is hydrogen.

83. The improved process according to claim 81 wherein $R_5$ is aryl or lower cycloalkyl.

84. The improved process according to claim 81 wherein $R_4$ is hydrogen and $R_5$ is aryl or lower cycloalkyl.

85. The improved process according to claim 84 wherein $R_5$ is phenyl or cyclopropyl.

86. The improved process according to claim 81 wherein dilute acid is used.

87. The improved process according to claim 86 wherein dilute trifluoracetic acid is used.

88. In a process for protecting the amino group on the side chain of a first compound consisting of an amino acid or peptide during peptide synthesis wherein the first compound is coupled via peptide linkage to a second compound consisting of a second amino acid or peptide under peptide forming conditions and the cycle repeated until the desired peptide has been obtained, the improvement comprising reacting the amino group on the side chain of the first compound with a cyclopropylmethyl compound of the formula:

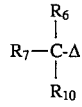

under substitution reaction conditions prior to said coupling wherein $R_6$ and $R_7$ are independently lower alkyl, aryl, aryl lower alkyl, lower cycloalkyl or cycloalkyl lower alkyl, and $R_{10}$ is a leaving group and (b) after the desired peptide is obtained removing the cyclopropylmethyl group from the amine.

89. The improved process according to claim 88 wherein $R_{10}$ is a halide, tosylate or mesylate.

90. The improved process according to claim 88 wherein $R_6$ and $R_7$ are independently lower alkyl.

91. The improved process according to claim 88 wherein $R_6$ and $R_7$ are methyl.

92. The improved process according to claim 88 wherein the first compound contains Lys, His, or Trp.

93. A process for protecting an amino acid residue containing an OH group in the side chain which comprises (a) reacting an alcohol of the formula:

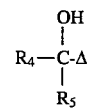

with a nitrile of the formula $R_{13}$ C≡N under effective conditions to form the corresponding imine ether of the formula:

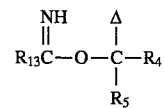

and (b) reacting the product of (a) with the amino acid residue containing the hydroxy group in the side chain to form the corresponding cyclopropylmethylether, wherein $R_{13}$ is lower alkyl which may be unsubstituted or substituted with lower alkyl or an electron donating or electron withdrawing group;

$R_4$ is hydrogen or lower alkyl; and $R_5$ is lower alkyl, aryl, aryl lower alkyl, lower cycloalkyl or lower cycloalkyl lower alkyl.

94. The process according to claim 93 wherein $R_{13}$ is $CCl_3$.

95. The process according to claim 93 wherein $R_4$ is hydrogen.

96. The process according to claim 93 wherein $R_5$ is aryl or lower cycloalkyl.

97. The process according to claim 93 wherein $R_4$ is hydrogen and $R_5$ is cyclopropyl or phenyl.

98. The process according to claim 93 wherein $R_5$ is cyclopropyl or phenyl.

99. A process for protecting a mercapto group on the side chain of a first compound selected from the group consisting of a first amino acid and a first peptide comprising (a) reacting said first compound with a cyclopropyl methanol of the formula:

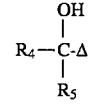

wherein $R_4$ is hydrogen or loweralkyl; and $R_5$ is lower alkyl, lower cycloalkyl, aryl lower alkyl, aryl, or lower cycloalkyl lower alkyl to form a cyclopropylmethyl protected mercapto group;

(b) reacting the product of (a) with a second compound selected from the group consisting of a second amino acid and second peptide under peptide forming conditions, and (c) removing the cyclopropylmethyl protecting group.

100. The process according to claim 99 wherein the first amino acid or peptide contains Cys.

101. A process for protecting a carboxy group on the side chain of an amino acid or peptide which comprises reacting said amino acid or peptide with a cyclopropyl methanol of the formula:

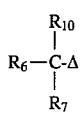

under esterification conditions, wherein $R_4$ is hydrogen or loweralkyl; and $R_5$ is lower alkyl, aryl lower alkyl, aryl, lower cycloalkyl, or lower cycloalkyl lower alkyl.

102. The process according to claim 101 wherein the amino acid is Glu or Asp.

103. A process for protecting an amino group on the side chain of an amino acid comprises reacting said amino acid with an effective amount of a compound under conditions effective to form a primary or secondary amine, said compound having the formula:

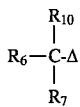

wherein $R_6$ and $R_7$ are independently lower alkyl, aryl, aryl lower alkyl, lowercycloalkyl or lower cycloalkyl lower alkyl and $R_{10}$ is a leaving group.

104. The process according to claim 103 wherein $R_{10}$ is halide, mesylate or tosylate.

105. A process for converting a carboxy group on a first amino acid or first peptide to an amide and protecting said amide which comprises:

(a) reacting said first amino acid or first peptide with a cyclopropylmethylamine of the formula:

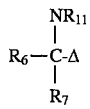

wherein $R_{11}$ is hydrogen or lower alkyl and $R_6$ and $R_7$ are independently lower alkyl, aryl, arylloweralkyl, lower cycloalkyl or lower cycloalkyl lower alkyl;

(b) reacting the product of (a) with a second amino acid or second peptide under amide forming conditions and (c) removing the protecting group on said amide.

106. The process according to claim 105 wherein the carboxy group is located on a side chain of the amino acid.

107. The process according to claim 105 wherein the amino acid is Asp or Glu.

108. The process according to claim 105 wherein the product formed is a cyclopropylmethylamide of Asn or Gln.

109. A process for protecting a primary or secondary amino group on an organic molecule during a reaction which modifies a portion of the molecule other than the protected amino group comprising:

(a) reacting the amino group with a compound of the formula:

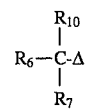

under effective conditions to react with said amino group, wherein $R_6$ and $R_7$ are independently lower alkyl, aryl, aryl lower alkyl, lower cycloalkyl or lower cycloalkyl lower alkyl and $R_{10}$ is a leaving group;

(b) modifying a portion of the molecule other than the protected amino group by chemical reaction; and (c) removing the protecting group from the carboxy group.

110. The process according to claim 109 wherein $R_{10}$ is halide, tosylate, mesylate or brosylate.

111. The process according to claim 109 wherein the amino group is located on the main or side chain of an amino acid or residue thereof.

112. The compound according to claim 1, 12 or 21 wherein BLK is CLIMOC, BIMOC, dbd-TMOC, BSPOC, BSMOC, FMOC, BOC, ACO, TEOC, ADOC, MCB, BPOC, AZOC, DDZ, POC, CBZ, TAC, NPS, DTS, phthaloyl, piperidinooxycarbonyl, FOC, MOZ, formyl acetyl or trifluoroacetyl.

* * * * *

UNITED STATES PATENT AND TRADEMARK OFFICE
CERTIFICATE OF CORRECTION

PATENT NO. : 5,536,815

DATED : July 16, 1996

INVENTOR(S) : Louis A. Carpino, et al.

It is certified that error appears in the above-indentified patent and that said Letters Patent is hereby corrected as shown below:

Column 9, line 59: "B- " should read -- $\beta$ - --

Column 15, line 31: "acid,." should read --acid,--

Column 18, line 23: "4" should read --(4)--

Column 19, line 8: Under the formula insert --7--

Column 19, line 11: "R6" should read --$R_6$--

Column 20, lines 39-40: "Cyclopropylmethyl" should read --cyclopropylmethyl--

Column 22, line 22: "$\delta$ 62.59" should read -- $\delta$ 2.59--

Column 31, line 4: "
$$-\underset{R_5}{\overset{R_4}{\underset{|}{\overset{|}{C}}}}- \Delta,$$
" should read -- $R_2$ is $-\underset{R_5}{\overset{R_4}{\underset{|}{\overset{|}{C}}}}- \Delta,$ --

UNITED STATES PATENT AND TRADEMARK OFFICE
CERTIFICATE OF CORRECTION

PATENT NO. : 5,536,815
DATED : July 16, 1996
INVENTOR(S) : Louis A. Carpino, et al.

It is certified that error appears in the above-indentified patent and that said Letters Patent is hereby corrected as shown below:

Column 31, lines 27-28, Claim 8: "aryl cylcoloweralkyl" should read --aryl, aryl lower alkyl--

Column 34, line 28, Claim 49: "α-amino" should read --α- --

Column 34, line 64, Claim 56: "α-amino" should read --α- --

Column 35, line 28, Claim 62: "α-amino" should read --α- --

Signed and Sealed this

Seventh Day of April, 1998

Attest:

BRUCE LEHMAN

*Attesting Officer*  *Commissioner of Patents and Trademarks*